(12) United States Patent
Patil et al.

(10) Patent No.: US 8,999,636 B2
(45) Date of Patent: Apr. 7, 2015

(54) REACTION CHAMBER

(75) Inventors: Vishal Patil, Corvallis, OR (US); Emilia Mollova, Mountain View, CA (US); Rudolf Gilmanshin, Framingham, MA (US)

(73) Assignee: Toxic Report LLC, Watertown, MA (US)

( * ) Notice: Subject to any disclaimer, the term of this patent is extended or adjusted under 35 U.S.C. 154(b) by 505 days.

(21) Appl. No.: 12/448,800

(22) PCT Filed: Jan. 8, 2008

(86) PCT No.: PCT/US2008/000293
§ 371 (c)(1),
(2), (4) Date: Dec. 10, 2009

(87) PCT Pub. No.: WO2008/085991
PCT Pub. Date: Jul. 17, 2008

(65) Prior Publication Data
US 2010/0120101 A1    May 13, 2010

Related U.S. Application Data

(60) Provisional application No. 60/879,148, filed on Jan. 8, 2007, provisional application No. 60/992,831, filed on Dec. 6, 2007.

(51) Int. Cl.
| C12Q 1/68 | (2006.01) |
| C12M 1/00 | (2006.01) |
| B01D 21/00 | (2006.01) |
| C12N 15/10 | (2006.01) |

(52) U.S. Cl.
CPC .................................. C12N 15/1003 (2013.01)

(58) Field of Classification Search
None
See application file for complete search history.

(56) References Cited

U.S. PATENT DOCUMENTS

| 3,954,621 A | 5/1976 | Etani et al. |
| 3,969,218 A | 7/1976 | Scott |
| 4,147,621 A | 4/1979 | Giddings |
| 4,545,888 A | 10/1985 | Walsh |
| 4,608,147 A | 8/1986 | Clad et al. |
| 4,617,102 A | 10/1986 | Tomblin et al. |
| 4,833,332 A | 5/1989 | Robertson, Jr. et al. |
| 4,964,961 A | 10/1990 | Brautigam et al. |
| 5,102,518 A | 4/1992 | Doering et al. |
| 5,126,022 A | 6/1992 | Soane et al. |
| 5,133,844 A * | 7/1992 | Stevens ........................ 204/549 |

(Continued)

FOREIGN PATENT DOCUMENTS

| EP | 1 380 337 A2 | 1/2004 |
| GB | 2148325 | 5/1985 |

(Continued)

OTHER PUBLICATIONS

Chan et al., DNA mapping technology based on microfluidic stretching and single-molecule detection of motif tags. Biophys J. 2003;84:302A. Poster 1470. Board #B725.

(Continued)

*Primary Examiner* — Betty Forman
(74) *Attorney, Agent, or Firm* — Wolf, Greenfield & Sacks, P.C.

(57) ABSTRACT

A chamber in which an agent, like genomic DNA, may be harvested and optionally manipulated rapidly (e.g., on the order of a few hours), without shearing or fragmentation.

14 Claims, 9 Drawing Sheets

(56) References Cited

U.S. PATENT DOCUMENTS

| | | | |
|---|---|---|---|
| 5,141,651 A | 8/1992 | Giddings | |
| 5,169,511 A | 12/1992 | Allington et al. | |
| 5,284,559 A | 2/1994 | Lim et al. | |
| 5,304,487 A | 4/1994 | Wilding et al. | |
| 5,318,680 A | 6/1994 | Fishman et al. | |
| 5,340,449 A | 8/1994 | Shukla | |
| 5,427,663 A | 6/1995 | Austin et al. | |
| 5,439,573 A | 8/1995 | Luo | |
| 5,449,917 A | 9/1995 | Clements | |
| 5,453,382 A | 9/1995 | Novotny et al. | |
| 5,505,831 A | 4/1996 | Liao et al. | |
| 5,601,694 A | 2/1997 | Maley et al. | |
| 5,674,743 A * | 10/1997 | Ulmer | 435/287.2 |
| 5,675,155 A | 10/1997 | Pentoncy, Jr. et al. | |
| 5,699,157 A | 12/1997 | Parce | |
| 5,711,861 A | 1/1998 | Ward et al. | |
| 5,711,868 A | 1/1998 | Maley et al. | |
| 5,733,442 A | 3/1998 | Shukla | |
| 5,766,435 A | 6/1998 | Liao et al. | |
| 5,798,215 A | 8/1998 | Cathey et al. | |
| 5,800,690 A | 9/1998 | Chow et al. | |
| 5,837,115 A | 11/1998 | Austin et al. | |
| 5,843,767 A | 12/1998 | Beattie | |
| 5,846,727 A | 12/1998 | Soper et al. | |
| 5,867,266 A | 2/1999 | Craighead | |
| 5,879,625 A | 3/1999 | Roslaniec et al. | |
| 5,880,473 A | 3/1999 | Ginestet | |
| 5,888,370 A | 3/1999 | Becker et al. | |
| 5,906,723 A | 5/1999 | Mathies et al. | |
| 5,942,093 A | 8/1999 | Rakestraw et al. | |
| 5,965,001 A | 10/1999 | Chow et al. | |
| 5,971,158 A | 10/1999 | Yager et al. | |
| 6,001,229 A | 12/1999 | Ramsey | |
| 6,008,892 A | 12/1999 | Kain et al. | |
| 6,013,164 A | 1/2000 | Paul et al. | |
| 6,019,882 A | 2/2000 | Paul et al. | |
| 6,071,394 A | 6/2000 | Cheng et al. | |
| 6,071,395 A | 6/2000 | Lange | |
| 6,090,251 A | 7/2000 | Sundberg et al. | |
| 6,100,541 A | 8/2000 | Nagle et al. | |
| 6,120,666 A | 9/2000 | Jacobson et al. | |
| 6,139,800 A | 10/2000 | Chandler | |
| 6,193,647 B1 | 2/2001 | Beebe et al. | |
| 6,210,896 B1 | 4/2001 | Chan | |
| 6,214,246 B1 | 4/2001 | Craighead | |
| 6,218,126 B1 | 4/2001 | Yasuda et al. | |
| 6,224,728 B1 | 5/2001 | Oborny et al. | |
| 6,232,464 B1 | 5/2001 | Lange | |
| 6,263,286 B1 | 7/2001 | Gilmanshin et al. | |
| 6,277,257 B1 | 8/2001 | Paul et al. | |
| 6,319,469 B1 | 11/2001 | Mian et al. | |
| 6,319,472 B1 | 11/2001 | Ackley et al. | |
| 6,355,420 B1 | 3/2002 | Chan | |
| 6,403,311 B1 | 6/2002 | Chan | |
| 6,413,401 B1 | 7/2002 | Chow et al. | |
| 6,428,666 B1 | 8/2002 | Singh et al. | |
| 6,432,630 B1 | 8/2002 | Blankenstein | |
| 6,444,992 B1 | 9/2002 | Kauvar et al. | |
| 6,489,112 B1 | 12/2002 | Hadd et al. | |
| 6,495,015 B1 | 12/2002 | Schoeniger et al. | |
| 6,506,609 B1 | 1/2003 | Wada et al. | |
| 6,562,307 B1 | 5/2003 | Schuch et al. | |
| 6,572,749 B1 | 6/2003 | Paul et al. | |
| 6,605,454 B2 | 8/2003 | Barenburg et al. | |
| 6,641,708 B1 | 11/2003 | Becker et al. | |
| 6,645,757 B1 | 11/2003 | Okandan et al. | |
| 6,660,480 B2 | 12/2003 | Ramsey et al. | |
| 6,696,022 B1 | 2/2004 | Chan et al. | |
| 6,762,059 B2 | 7/2004 | Chan et al. | |
| 6,767,731 B2 | 7/2004 | Hannah et al. | |
| 6,770,182 B1 | 8/2004 | Griffiths et al. | |
| 6,770,201 B2 | 8/2004 | Sheppod et al. | |
| 6,772,070 B2 | 8/2004 | Gilmanshin et al. | |
| 6,790,671 B1 | 9/2004 | Austin et al. | |
| 6,818,113 B2 | 11/2004 | Williams et al. | |
| 6,866,759 B2 | 3/2005 | Miles et al. | |
| 6,890,411 B1 | 5/2005 | Hayes et al. | |
| 6,914,137 B2 | 7/2005 | Baker | |
| 6,927,065 B2 | 8/2005 | Chan et al. | |
| 6,943,009 B2 | 9/2005 | Lacey et al. | |
| 6,949,355 B2 | 9/2005 | Yamanishi et al. | |
| 6,960,285 B2 | 11/2005 | Schoeniger et al. | |
| 6,998,598 B2 | 2/2006 | Horn et al. | |
| 7,014,747 B2 | 3/2006 | Cummings et al. | |
| 7,052,608 B2 | 5/2006 | Shepodd et al. | |
| 7,094,345 B2 | 8/2006 | Gilbert et al. | |
| 7,262,859 B2 | 8/2007 | Larson et al. | |
| 7,282,330 B2 | 10/2007 | Zhao et al. | |
| 7,332,126 B2 | 2/2008 | Tooke et al. | |
| 7,351,538 B2 | 4/2008 | Fuchs et al. | |
| 7,371,520 B2 | 5/2008 | Zhao et al. | |
| 7,402,422 B2 | 7/2008 | Fuchs et al. | |
| 7,595,160 B2 | 9/2009 | White et al. | |
| 7,648,677 B2 | 1/2010 | Santini, Jr. et al. | |
| 7,828,948 B1 * | 11/2010 | Hatch et al. | 204/455 |
| 7,888,011 B2 | 2/2011 | Nilsen et al. | |
| 7,977,048 B2 | 7/2011 | Gilmanshin | |
| 8,114,636 B2 | 2/2012 | Agnew et al. | |
| 8,168,380 B2 | 5/2012 | Chan | |
| 8,361,716 B2 | 1/2013 | Patil | |
| 8,423,294 B2 | 4/2013 | Nadel et al. | |
| 8,685,708 B2 | 4/2014 | Harris et al. | |
| 2001/0030130 A1 | 10/2001 | Ricco et al. | |
| 2001/0055817 A1 | 12/2001 | Malmqvist et al. | |
| 2002/0008028 A1 | 1/2002 | Jacobson et al. | |
| 2002/0029814 A1 | 3/2002 | Unger et al. | |
| 2002/0034748 A1 | 3/2002 | Quake et al. | |
| 2002/0055167 A1 | 5/2002 | Pourahmadi et al. | |
| 2002/0058332 A1 | 5/2002 | Quake et al. | |
| 2002/0072243 A1 | 6/2002 | Craighead et al. | |
| 2002/0079008 A1 | 6/2002 | Chien et al. | |
| 2002/0109844 A1 | 8/2002 | Christel et al. | |
| 2002/0110495 A1 | 8/2002 | Hunt et al. | |
| 2002/0110818 A1 | 8/2002 | Chan | |
| 2002/0119455 A1 | 8/2002 | Chan | |
| 2002/0187508 A1 | 12/2002 | Wong | |
| 2002/0197639 A1 | 12/2002 | Shia et al. | |
| 2003/0008320 A1 | 1/2003 | Baker | |
| 2003/0010637 A1 | 1/2003 | Cummings | |
| 2003/0054395 A1 | 3/2003 | Baker | |
| 2003/0058440 A1 | 3/2003 | Scott et al. | |
| 2003/0059822 A1 | 3/2003 | Chan et al. | |
| 2003/0104466 A1 | 6/2003 | Knapp et al. | |
| 2003/0124623 A1 | 7/2003 | Yager et al. | |
| 2003/0130499 A1 | 7/2003 | Baker | |
| 2003/0134416 A1 * | 7/2003 | Yamanishi et al. | 435/372 |
| 2003/0162181 A1 | 8/2003 | Yang et al. | |
| 2003/0215864 A1 | 11/2003 | Gilmanshin et al. | |
| 2003/0235854 A1 | 12/2003 | Chan et al. | |
| 2004/0000519 A1 | 1/2004 | Jiang et al. | |
| 2004/0028580 A1 | 2/2004 | Futami et al. | |
| 2004/0053399 A1 | 3/2004 | Gilmanshin | |
| 2004/0084370 A1 | 5/2004 | Singh et al. | |
| 2004/0126279 A1 | 7/2004 | Renzi et al. | |
| 2004/0166025 A1 | 8/2004 | Chan et al. | |
| 2004/0188254 A1 | 9/2004 | Spaid | |
| 2004/0211669 A1 | 10/2004 | Cummings et al. | |
| 2004/0214211 A1 | 10/2004 | Gilmanshin et al. | |
| 2004/0235014 A1 | 11/2004 | Nadel et al. | |
| 2005/0009066 A1 | 1/2005 | Connolly | |
| 2005/0042665 A1 | 2/2005 | Gilmanshin et al. | |
| 2005/0112606 A1 | 5/2005 | Fuchs et al. | |
| 2005/0112620 A1 | 5/2005 | Chan | |
| 2005/0112671 A1 | 5/2005 | Maletta et al. | |
| 2005/0123944 A1 | 6/2005 | Neely et al. | |
| 2005/0123974 A1 | 6/2005 | Gilmanshin et al. | |
| 2005/0142565 A1 | 6/2005 | Samper et al. | |
| 2005/0142595 A1 | 6/2005 | Maletta et al. | |
| 2005/0148064 A1 * | 7/2005 | Yamakawa et al. | 435/287.2 |
| 2005/0153354 A1 | 7/2005 | Gilmanshin | |
| 2005/0173315 A1 * | 8/2005 | Bosch et al. | 210/97 |
| 2005/0191760 A1 | 9/2005 | Heath et al. | |
| 2005/0196790 A1 | 9/2005 | Rooke | |
| 2005/0221408 A1 | 10/2005 | Nalefski et al. | |

(56) References Cited

U.S. PATENT DOCUMENTS

| | | |
|---|---|---|
| 2006/0134679 A1 | 6/2006 | Larson |
| 2006/0160231 A1 | 7/2006 | Nadel et al. |
| 2006/0191792 A1 | 8/2006 | Herr et al. |
| 2006/0194306 A1 | 8/2006 | Herr et al. |
| 2006/0204978 A1 | 9/2006 | Nilsen et al. |
| 2006/0211055 A1 | 9/2006 | Hafeman et al. |
| 2006/0292616 A1 | 12/2006 | Neely et al. |
| 2006/0292617 A1 | 12/2006 | Neely et al. |
| 2007/0031961 A1 | 2/2007 | Ho et al. |
| 2007/0042406 A1 | 2/2007 | Yantz et al. |
| 2007/0117092 A1 | 5/2007 | Sadarangani et al. |
| 2007/0128083 A1 | 6/2007 | Yantz et al. |
| 2007/0166743 A1 | 7/2007 | Gilmanshin |
| 2008/0003689 A1 | 1/2008 | Lee et al. |
| 2008/0085552 A1 | 4/2008 | Larson et al. |
| 2008/0103296 A1 | 5/2008 | Zhao et al. |
| 2008/0254549 A1 | 10/2008 | Fuchs et al. |
| 2008/0280285 A1 | 11/2008 | Chen et al. |
| 2009/0035770 A1 | 2/2009 | Mathies et al. |
| 2009/0325269 A1 | 12/2009 | Marschke |
| 2010/0035247 A1 | 2/2010 | Burton et al. |
| 2010/0112576 A1 | 5/2010 | Patil |
| 2010/0116025 A1 | 5/2010 | Gouveia et al. |
| 2010/0120101 A1 | 5/2010 | Patil et al. |
| 2010/0234237 A1 | 9/2010 | Yoo |
| 2010/0294665 A1 | 11/2010 | Allen et al. |
| 2012/0283955 A1 | 11/2012 | Cameron et al. |
| 2013/0000738 A1 | 1/2013 | Krogmeier et al. |
| 2013/0266935 A1 | 10/2013 | Patil |
| 2013/0288234 A1 | 10/2013 | Harris et al. |
| 2013/0295686 A1 | 11/2013 | Meltzer et al. |
| 2013/0309780 A1 | 11/2013 | Meltzer et al. |
| 2014/0011686 A1 | 1/2014 | Gilmanshin |

FOREIGN PATENT DOCUMENTS

| | | |
|---|---|---|
| JP | 63-196845 A | 8/1988 |
| JP | 3075602 | 3/1991 |
| JP | 5072178 | 3/1993 |
| JP | 5223778 | 8/1993 |
| JP | 8327595 | 12/1996 |
| JP | 2005-181204 | 7/2005 |
| WO | WO 94/16313 A2 | 7/1994 |
| WO | WO 98/30571 A1 | 7/1998 |
| WO | WO 98/35012 A2 | 8/1998 |
| WO | WO 99/09042 A2 | 2/1999 |
| WO | WO 00/50172 A1 | 8/2000 |
| WO | WO 00/56444 A2 | 9/2000 |
| WO | WO 00/70080 A1 | 11/2000 |
| WO | WO 01/28700 A1 | 4/2001 |
| WO | WO 02/29106 A2 | 4/2002 |
| WO | WO 03/000416 A2 | 1/2003 |
| WO | WO 2004/076692 A1 | 9/2004 |
| WO | WO 2005/078137 A1 | 8/2005 |
| WO | WO 2005/085849 A2 | 9/2005 |
| WO | WO2006/017274 * | 2/2006 |
| WO | WO 2008/024483 A1 | 2/2008 |
| WO | WO 2008-085991 A2 | 7/2008 |
| WO | WO 2008-111959 A2 | 9/2008 |
| WO | WO 2009/009127 A2 | 1/2009 |
| WO | WO 2010-149292 A1 | 12/2010 |
| WO | WO 2011-102804 A1 | 8/2011 |

OTHER PUBLICATIONS

Chan et al., DNA mapping using microfluidic stretching and single-molecule detection of fluorescent site-specific tags. Genome Res. Jun. 2004;14(6):1137-46.

D'Antoni et al., Single Molecule Detection of Proteins Using Microfluidic Fluorescence Detection. ORC Poster. Apr. 2006.

Duke et al., Microfabricated sieve for the continuous sorting of macromolecules. Phys. Rev. Lett. 1998; 80:1552-1555. Abstract Only.

Ertas, Lateral separation of macromolecules and polyelectrolytes in microlithographic arrays. Phys. Rev. Lett. 1998; 80:1548-1551. Abstract Only.

Larson et al., Single DNA molecule stretching in sudden mixed shear and elongational microflows. Lab Chip. 2006;6(9):1187-1199.

Phillips et al., Application of single molecule technology to rapidly map long DNA and study the confirmation of stretched DNA. Nuc Acids Res. 2005;33(18):5829-5837.

Shera et al., Detection of single fluorescent molecules. Chem Phys Letts. Nov. 23, 1990;174(6):553-7.

[No Author Listed] FRAEN FLP Series Lenses for Luxeon LEDs: Luxeon I, III, and V, Star and Emitter. Jan. 4, 2005. Available at http://www.fraensrl.com/images/FLP_Lens_Series_Datasheet.pdf. 8 pages.

[No Author Listed] Figure 5. Physics Today Online. Available at http://www.physicstoday.org/pt/vol-54/iss-6/captions/p42cap5.html. Last accessed Jul. 15, 2002. 2 pages.

Agronskaia et al. Two-color fluorescence in flow cytometry DNA sizing: Identification of single-molecule fluorescent probes. Anal. Chem. 1999;71:4684-4689. Abstract.

Ashworth. et al., Transducer mechanisms for optical biosensors. Part 2: Transducer design. Comput Methods Programs Biomed. Sep. 1989;30(1):21-31.

Boone et al., Plastic advances microfluidic devices. Anal Chem. Feb. 1, 2002;74(3):78A-86A.

Burns et al., An integrated nanoliter DNA analysis device. Science. Oct. 16, 1998;282(5388):484-7. (Abstract Only).

Cheek et al., Chemiluminescence detection for hybridization assays on the flow-thru chip, a three-dimensional microchannel biochip. Anal Chem. Dec. 15, 2001;73(24):5777-83.

Chou et al., A microfabricated device for sizing and sorting DNA molecules. Proc Natl Acad Sci U S A. Jan. 5, 1999;96(1):11-13.

Cova et al., Evolution and prospects for single-photon avalanche diodes and quenching circuits. J Mod Opt. Jun.-Jul. 2004;51(9-10):1267-88.

Dittrich et al., Sorting of cells and single particles in microstructures. Biophys J. 2002;82:43a. 209-Pos. Board # B70.

Foquet et al., DNA fragment sizing by single molecule detection in submicrometer-sized closed fluidic channels. Anal Chem. Mar. 15, 2002;74(6):1415-22. (Abstract Only).

Giddings et al., Chapter 1. The Field-Flow Fractionation Family: Underlying Principles. In: Field-Flow Fractionation Handbook. Wiley-Interscience. 2000: 3-30.

Han et al., Separation of long DNA molecules in a microfabricated entropic trap array. Science. May 12, 2000;288(5468):1026-9.

Harrison et al., Capillary Electrophoresis and Sample Injection Systems Integrated on a Planar Glass Chip, Anal. Chem. 1992; 64:1926, First Page Only.

Krogmeier et al., A Microfluidic Device for Concentrating High Molecular Weight DNA. Mar. 2, 2009; 315a. 1608 Pos. Board B452. Abstract Only.

Kwok et al., An Integrated Multifunction Lab-on-a-Chip Platform for Hugh Throughput Optical Mapping for DNA. Nanotechnology. 2009;48a. 244-Pos. Board B123. Abstract Only.

Kwok et al., An Integrated Multifunction Lab-on-a-Chip Platform for Hugh Throughput Optical Mapping for DNA. Biophysical Society 53rd Annual Meeting. Feb. 28-Mar. 4, 2009. Boston. Poster.

Lee et al., Analysis of self-assembled cationic lipid-DNA gene carrier complexes using flow field-flow fractionation and light scattering. Anal Chem. Feb. 15, 2001;73(4):837-43.

Lee et al., Micro flow cytometers with buried SU-8/SOG optical waveguides. Sensors and Actuators. 2003;103:165-70.

Lee et al., Mircomachined pre-focused M x N flow switches for continuous multi-sample injection, J Micromech Microeng. 2001;11:654-661.

Li et al., Chapter 28. Protein Complexes and Lipoproteins. In: Field Flow Fractionation Handbook. Wiley-Interscience. 2000: 433-470.

Lyon et al., 1997, "Confinement and detection of single molecules in submicrometer channels", Anal. Chem. 69:3400-3405. Abstract.

Meltzer et al., A lab-on-chip for biothreat detection using single-molecule DNA mapping. Lab Chip. Mar. 7, 2011;11(5):863-73. Epub Jan. 20, 2011.

Mollova et al., An automated sample preparation system with mini-reactor to isolate and process submegabase fragments of bacterial DNA. Anal Biochem. Aug. 15, 2009;391(2):135-43. Epub May 12, 2009.

(56) References Cited

OTHER PUBLICATIONS

Nie et al., Probing individual molecules with confocal fluorescence microscopy. Science. Nov. 11, 1994;266(5187):1018-21.
Papkov et al., A single-molecule system for detection and quantification of proteins with robust capture units and potential for high multiplexing. Biophysical Society 53rd Annual Meeting. Feb. 28-Mar. 4, 2009. Boston. Poster.
Pasquinelli et al., Control of developmental timing by micrornas and their targets. Annu Rev Cell Dev Biol. 2002;18:495-513. Epub Apr. 2, 2002. Abstract.
Protozanova et al., Binding Specificity of Multi-Labeled PNA Probes Studied by Single Molecule Mapping. Biophysical Society 53rd Annual Meeting. Feb. 28-Mar. 4, 2009. Boston. 25a. 124-Pos. Board B3. Abstact.
Protozanova et al., Fast high-resolution mapping of long fragments of genomic DNA based on single-molecule detection. Anal Biochem. Jul. 1, 2010;402(1):83-90. Epub Mar. 20, 2010.
Protozanova et al., Fast high-resolution mapping of long fragments of genomic DNA based on single-molecule detection. Anal Biochem. Jul. 1, 2010;402(1):83-90. Epub Mar. 20, 2010. Supplemental Data.
Radcliff et al., Chapter 1. Basics of flow cytometry. In: Methods Mol Biol. 1998;91:1-24.
Roulet et al., Fabrication of multilayer systems combining microfluidic and microoptical elements for fluorescence detection. J Micro Systms. Dec. 2001;10(4):482-91.
Roulet et al., Performance of an integrated microoptical system for fluorescence detection in microfluidic systems. Anal Chem. Jul. 15, 2002;74(14):3400-7.
Schmalzing et al., 1997, "DNA typing in thirty seconds with a microfabricated device", Proc. Natl. Acad. Sci. USA 94:10273-10278.
Schmalzing et al., 1998, "DNA sequencing on microfabricated electrophoretic devices", Anal. Chem. 70:2303-2310. Abstract Only.
Soper et al., Nanoliter-scale sample preparation methods directly coupled to polymethylmethacrylate-based microchips and gel-filled capillaries for the analysis of oligonucleotides. J Chromatography A. 1999;853:107-20.
Wabuyele et al., Single molecule detection of double-stranded DNA in poly(methylmethacrylate) and polycarbonate microfluidic devices. Electrophoresis. Oct. 2001;22(18):3939-48. (Abstract Only).
Wahlund et al., Application of an asymmetrical flow field-flow fractionation channel to the separation and characterization of proteins, plasmids, plasmid fragments, polysaccharides and unicellular algae. J Chromatogr. Jan. 6, 1989;461:73-87.
Washizu et al., 1990, "Electrostatic manipulation of DNA in microfabricated structures", IEEE Trans Industry Applications 26:1165-1172. Abstract.
Watson et al., The early fluidic and optical physics of cytometry. Cytometry. Feb. 15, 1999;38(1):2-14.
White et al., *Staphylococcus aureus* strain typing by single-molecule DNA mapping in fluidic microchips with fluorescent tags. Clin Chem. Dec. 2009;55(12):2121-9. Epub Oct. 8, 2009.
White et al., *Staphylococcus aureus* strain typing by single-molecule DNA mapping in fluidic microchips with fluorescent tags. Clin Chem. Dec. 2009;55(12):2121-9. Epub Oct. 8, 2009. Supplemental Data.
Whitesides et al., Devices for handling nanoliter qualities of fluids are creating new fabrication challenges and finding new applications in biology, chemistry, and materials science. Physics Today Online. Jun. 2001, 8 pages.
Whitesides et al., Generating Microgradients. Harvard MRSEC—Research Nuggets. Materials Research Science and Engineering Center. Feb. 2, 2001. Available at http://www.mrsec.harvard.edu/research/nugget_4.html. Last accessed Jul. 15, 2002. 1 page.
Whitesides, Fabrication of Complex, 3D Microstructures, Harvard MRSEC—Research Nuggets. Materials Research Science and Engineering Center. Available at http://www.mrsec.harvard.edu/research/nugget_3.html. Last accessed Jul. 15, 2002. 1 page.
Whitesides, Three-Dimensional Networks of Fluid Channels in PDMS. Harvard MRSEC—Research Nuggets. Materials Research Science and Engineering Center. Jun. 1, 2000. Available at http://www.mrsec.harvard.edu/research/nugget_11.html. Last accessed Jul. 15, 2002. 1 page.
Wilding, et al Manipulation and flow of biological fluids in straight channels micromachined in silicon. Clin. Chem. 1994, vol. 40, No. 1, pp. 43-47. Abstract.
Wong et al., 2002, "Direct Manipulations of DNA Molecules Using Hydrodynamic Force", 2002 IEEE International Conference on Robotics and Automation, Washington D.C.
[No Author Listed], Simultaneous DNA Stretching and Intercalation in Continuous Elongational Flow. Poster abstract. 58th Annual Meeting of the Biophysical Society. Feb. 2014. 1 Page.
Bender et al., Surveillance for *Escherichia coli* O157:H7 infections in Minnesota by molecular subtyping. N Engl J Med. Aug. 7, 1997;337(6):388-94.
Burton et al., A microfluidic chip-compatible bioassay based on single-molecule detection with high sensitivity and multiplexing. Lab Chip. Apr. 7, 2010;10(7):843-51. Epub Jan. 14, 2010.
Kumar et al., Evaluation of genome sequence scanning technology for molecular (sub)-serotyping of *Salmonella* and simultaneous detection of multiple *Salmonella* serovars in complex mixtures. 4th Am Soc for Microbiol (ASM) Meeting on *Salmonella*. Oct. 9, 2013. Poster. 1 Page.
Kumar et al., Molecular serotyping and sub-typing of *Salmonella* strains by genome sequence scanning. Int'l Assoc for Food Protect Ann Mtg. Jul. 31, 2013. Poster. 1 Page.
Kumar et al., Molecular strain typing of Shiga-toxigenic *E. coli* (STEC) by genome sequence scanning. Assoc Pub Health Lab Gen Mtg. Jun. 2, 2013. 1 Page.
Kumar et al., Molecular strain typing of Shiga-toxigenic *E. coli* (STEC) by genome sequence scanning. Am Soc for Microbiol Gen Mtg. May 20, 2013. Poster. 1 Page.
Liu et al., Separation and Measurement of Diffusion Coefficients of Linear and Circular DNAs by Flow Field-Flow Fractionation. Macromolecules. 1993; 26(14):3576-88.
Malkin et al., Rapid detection and sub-serotype level typing of bacterial organisms using optical genome sequence scanning. Am Soc Microbiol Gen Meeting. 2013. Poster. 1 Page.
Noller et al., Multilocus sequence typing reveals a lack of diversity among *Escherichia coli* O157:H7 isolates that are distinct by pulsed-field gel electrophoresis. J Clin Microbiol. Feb. 2003;41(2): 675-9.
Pouseele et al., An Integrated Rapid Strain Typing Solution Combined With a Polyphasic Bioinformatics Tool has the Potential to Considerably Reduce the Time for Routine Outbreak Detection. InFORM 2013: Integrated Foodborne Outbreak Response and Management Meeting. Nov. 19, 2013. Poster. 1 Page.
Ramaswamy et al., Confirmation and typing of *Salmonella* by genome sequence scanning in presumptive positive food samples. Pathogenetix Poster. Jul. 30, 2013. 1 Page.
Ramaswamy et al., Rapid strain typing of *Salmonella* in food in the presence of competing microflora by genome sequence scanning. Am Soc Microbiol Gen Mtg. May 29, 2013. Poster. 1 Page.

\* cited by examiner

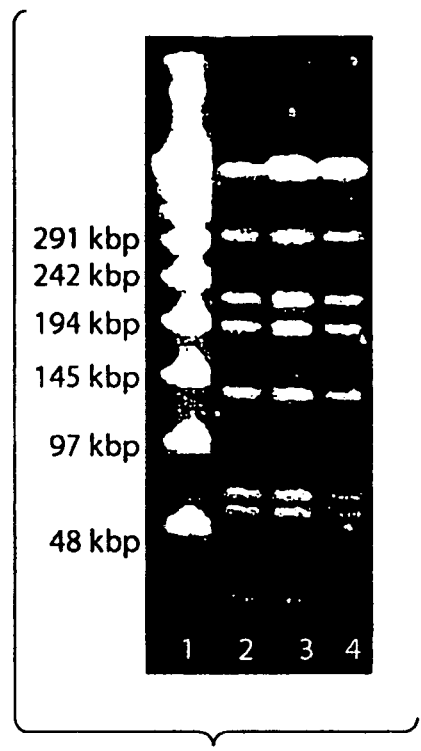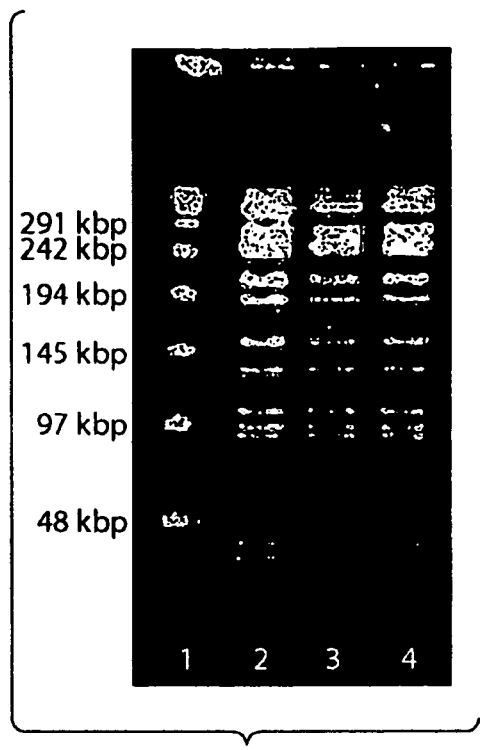
Fig. 7A  Fig. 7B
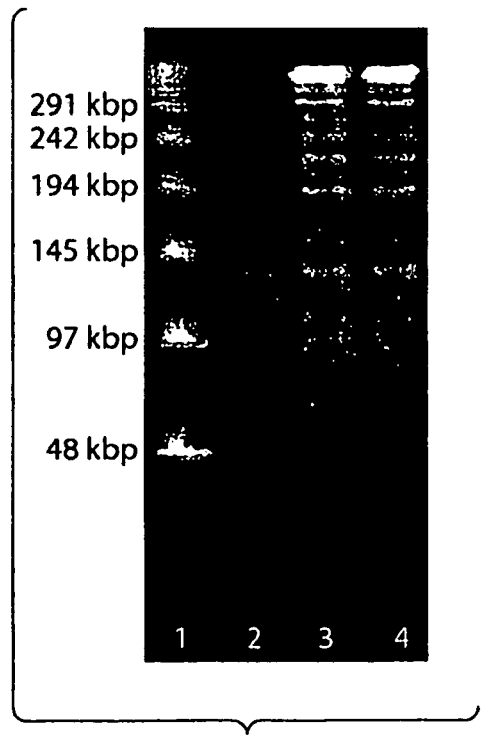
Fig. 7C

REACTION CHAMBER

RELATED APPLICATIONS

This application is a national stage filing under 35 U.S.C. §371 of international application PCT/US2008/000293, filed on Jan. 8, 2008, which was published under PCT Article 21(2) in English, and which claims the benefit under 35 U.S.C. §119(e) to U.S. Provisional Application Ser. No. 60/879,148, filed on Jan. 8, 2007, and to U.S. Provisional Application Ser. No. 60/992,831, filed on Dec. 6, 2007, the entire contents of all of which are incorporated by reference herein.

FEDERALLY SPONSORED RESEARCH

This invention was made with Government support under the Homeland Security Advanced Research Projects Agency, Contract No. W81XWH-04-9-0011. The Government has certain rights to this invention.

BACKGROUND

1. Field

Aspects of the invention relate to devices and methods of use thereof for harvesting, isolating, and/or manipulating agents, including but not limited to genomic DNA.

2. Discussion

Preparation and concomitant preservation of genomic DNA, according to many conventional techniques, is often time consuming, laborious and may require operators to have skills in handling DNA samples. Moreover such techniques are limited in the size of DNA that can be effectively handled. There exists a need to reduce the time, labor, and/or skills required to prepare essentially intact genomic DNA and other agents of similar length

SUMMARY

The invention in its broadest sense provides devices and methods of use thereof for harvesting, isolating, purifying, and/or manipulating agents, including but not limited to polymers such as genomic DNA. The invention allows very long polymers to be manipulated rapidly, compared to prior art manipulation methods, without loss of integrity (e.g., in the case of genomic DNA without shearing or unintended fragmentation or cleavage). The end result is the ability to harvest and manipulate, for example, DNA on the order of tens or hundreds of kilobases, or even megabases, in relatively short periods of time (i.e., on the order of a few hours). In still other important aspects, the devices and the methods they perform can be automated requiring little operator involvement and/or oversight. These and other aspects and embodiments will be discussed in greater detail herein.

Certain aspects of the invention relate to using a chamber for manipulating an agent, such as genomic DNA. In some aspects, the chamber is minimally comprised of an inlet port, a porous substrate that allows fluid but not the agents of interest to pass through, and at least one side port. Fluid flow is used to introduce, manipulate, separate, remove and/or harvest agents and/or other constituents from the chamber. As an example, the chamber is able to concentrate an agent in a particular volume of a flow region in the chamber, by spreading agents evenly across a substrate in the chamber, and/or by separating an agent from other constituents in chamber.

The chamber may be operated in several different modes, including a "press-down" mode where agents are positioned about a substrate in the chamber, a separation mode where agents are retained in the chamber while removing other constituents, an elution mode where agents are removed from the chamber, a reacting mode where agents are reacted with other constituents, and/or a focusing mode where agents are positioned in a central portion of a substrate or flow that exits the chamber.

Thus, in one aspect, the invention provides a reaction chamber and method for harvesting and/or manipulating agents rapidly, optionally wherein the harvesting and/or manipulating is automated. In various embodiments, harvesting and/or manipulating occurs in 12 hours or less, 10 hours or less, 8 hours or less, 6 hours or less, 4 hours or less, or 2 hours or less.

In another aspect, the invention provides a reaction chamber and method for harvesting and/or manipulating intact nucleic acids having a length of at least 150 kilobases, at least 500 kilobases, at least 1 megabase, or at least 5 megabases. In some embodiments, the nucleic acids are less than 10 megabases, less than 5 megabases, less than 1 megabase or less than 500 kilobases in length.

In another aspect, the invention provides a reaction chamber and method for harvesting and/or manipulating intact nucleic acids having a length of at least 50 kilobases in 12 hours or less. In one embodiment, the method is automated.

In another aspect, the invention provides a reaction chamber for manipulating intact nucleic acids having a length of at least 50 kilobases comprising a substrate; an inlet port positioned to direct fluid flow toward the substrate; and at least one side port. The reaction chamber may alternatively be used to harvest and/or manipulate agents in less than 12 hours, optionally by automation. In one embodiment, the substrate is positioned in close proximity to a reservoir. As an example, the substrate may be overlayed on the reservoir or supported by the reservoir.

In another aspect, the invention provides a method for manipulating a nucleic acid comprising harvesting a nucleic acid from a cell and manipulating the nucleic acid in a single chamber in the absence of shearing and/or deliberate (or intentional) fragmentation or cleavage, wherein the nucleic acid is at least 50 kilobases in length. Various embodiments of the invention comprise the deliberate fragmentation or cleavage of the nucleic acid (e.g., a restriction enzyme analysis) however this is not to be confused with the ability of the chamber, system and method to otherwise harvest and/or manipulate nucleic acids that are at least 50 kilobases in length. It is the ability of the chamber, system and method to harvest and/or manipulate the nucleic acids in an intact manner that allows analyses such as restriction analyses to occur.

In still another aspect, the invention provides a method for manipulating an agent such as a nucleic acid comprising harvesting an agent such as a nucleic acid from a cell and manipulating the agent such as a nucleic acid in a single chamber, wherein the agent such as the nucleic acid is harvested and manipulated in 12 hours or less, 10 hours or less, 8 hours or less, 6 hours or less, 4 hours or less, or 2 hours or less.

In various embodiments of the invention, the agents are proteins, peptides, nucleic acids, polysaccharides, lipids, or other naturally or non-naturally occurring polymers.

In various embodiments of the invention, the nucleic acids have a length of at least 100 kilobases, at least 150 kilobases, at least 250 kilobases, at least 500 kilobases, at least 750 kilobases, at least 1 megabase or at least 5 megabases in length. Nucleic acids in the range of about 50 kilobases to about 5 megabases, about 100 kilobases to about 5 megabases, about 150 kilobases to about 5 megabases, about 500 kilobases to about 5 megabases, about 500 megabases to 1 megabase, about 100 kilobases to about 1 megabase, or about 100 kilobases to about 500 kilobases are harvested and/or manipulated.

In various embodiments of the invention, the agent is harvested and manipulated in 12 hours or less, 10 hours or less, 8 hours or less, 6 hours or less, 4 hours or less, or 2 hours or less.

In various embodiments of the reaction chamber and method of use, the substrate is a membrane or other porous solid that preferably selectively retains agents of interest. The at least one side port may be two or more side ports (exit ports) including but not limited to 2, 3, 4, 5, 6, 7, 8, 9, 10, 11, 12, 13, 14, 15, 16, or more side ports.

In various embodiments of the invention, the methods of the invention are automated and/or the chambers are operated in an automated manner.

In various embodiments of the invention, manipulating the nucleic acid comprises hybridizing a sequence specific probe to the nucleic acid. In some embodiments, manipulating the nucleic acid comprises binding a backbone stain such as an intercalator to the nucleic acid. In some embodiments, manipulating the nucleic acid comprises exposing the nucleic acid to an exonuclease or endonuclease, including but not limited to a restriction endonuclease.

According to another aspect of the invention, a method is disclosed for separating agents from other constituents in fluid. The method comprises flowing fluid toward a substrate in a chamber through a fluid introduction port. The substrate is configured to prevent the passage of agents that are larger than a threshold size of the substrate. A first portion of the fluid flows through the substrate and out of the chamber. Agents and at least some of the other constituents are retained in proximity to the substrate with flow of the first portion of fluid through the substrate. A second portion of the fluid flows through one or more fluid exit ports. At least a portion of the other constituents move away from the substrate, into the flow of the second portion of fluid, and out of the chamber through the one or more fluid exit ports to separate the agents from the other constituents.

According to another embodiment, a system for separating agents from non-agents in a chamber is disclosed. The system comprises a chamber that includes a fluid introduction port. A substrate is positioned substantially opposite from the fluid introduction port in the chamber. The substrate is configured to prevent the passage of agents that are larger than a threshold size of the substrate. One or more fluid exit ports are positioned peripherally about the chamber between the fluid introduction port and the substrate. The system also comprises a controller that is configured to control a first flow of fluid into the chamber from the fluid introduction port and through the substrate to hold agents and other constituents at the substrate. The controller also controls a second flow of fluid into the chamber from the fluid introduction port and through the one or more fluid exit ports and a ratio between the first flow and the second flow allows other constituents to move away from the substrate and into the second flow to separate agents and the other constituents.

In one embodiment, fluid that contains the agents flows into the chamber from the fluid introduction port and through the substrate while preventing flow through the one or more fluid exit ports. The fluid that contains the agents may flow through a diffuser to distribute the agents about the substrate.

In one embodiment, the second portion of fluid may flow through the one or more fluid exit ports at an increased rate to remove the agents from the substrate and out of the chamber through the one or more fluid exit ports.

In one embodiment, fluid may flow out of the fluid introduction port to remove the agents from the chamber.

In one embodiment, the agents are genomic DNA and the other constituents comprise cellular debris released during cell lysis.

In one embodiment, fluid that contains cells flows into the chamber from the fluid introduction port and through the substrate while flow is prevented through the one or more fluid exit ports. Fluid that contains lytic enzymes may flow into the chamber from the fluid introduction port and through the substrate while flow is prevented through the one or more fluid exit ports. Flow may be substantially prevented from flowing through the chamber to allow lysis of the cells to occur.

In one embodiment, the agents are genomic DNA and the other constituents comprise endonucleases and/or exonucleases. Fluid that contains endonucleases and/or exonucleases may flow into the chamber from the fluid introduction port and through the substrate while flow is prevented through the one or more fluid exit ports. Flow may be prevented through the chamber to allow the DNA to be cleaved by the endonucleases and/or exonucleases.

In one embodiment, the agents are nucleic acids and the other constituents comprise probes that bind to the nucleic acids in a sequence-specific manner. Fluid that contains the probes may flow into the chamber from the fluid introduction port and through the substrate while flow through the one or more fluid exit ports is prevented. Flow may be substantially prevented through the chamber to allow the probes to bind in a sequence-specific manner to nucleic acids in the chamber.

In one embodiment, the agents are proteins and the other constituents comprise serum. The proteins and serum may flow into the chamber from the fluid introduction port and through the substrate while flow through the one or more fluid exit ports is prevented.

In one embodiment, the second portion of the fluid flows outward toward the one or more fluid exit ports. The one or more fluid exit ports may be 2 or more fluid exit ports, 4 or more fluid exit ports, 6 or more fluid exit ports, 8 or more fluid exit ports, 10 or more fluid exit ports, 12 or more fluid exit ports, 14 or more fluid exit ports, or 16 or more fluid exit ports, 3 or more fluid exit ports, 5 or more fluid exit ports, 7 or more fluid exit ports, 9 or more fluid exit ports, 11 or more fluid exit ports, 13 or more fluid exit ports, or 15 or more fluid exit ports. The one or more fluid exit ports may be positioned symmetrically about the chamber.

In one embodiment, fluid that flows toward the substrate may flow through a diffuser that is substantially opposed to the substrate.

In one embodiment, the first portion of the fluid may flow out of the chamber, and the second portion of the fluid may flow out of the chamber automatically.

According to another aspect of the invention, a method is disclosed for positioning agents in a fluid flow. The method comprises providing a chamber having a substrate and a diffuser. A first fluid containing agents flows through a first fluid port, the diffuser and through the substrate in the chamber. A second fluid flow flows through one or more second fluid ports positioned about the substrate in the chamber. The second fluid flow surrounds the first fluid flow to direct the first fluid flow and any agents contained therein toward a central portion of the substrate.

In one embodiment, flow through the first fluid port is reversed to move any agents positioned on the substrate out of the chamber in streamlines that flow through a central portion of the first fluid port. Flow through the second ports may be prevented when reversing flow through the first fluid port.

According to yet another aspect of the invention, a method of positioning agents in a fluid flow is disclosed. The method comprises providing a chamber having a substrate and a diffuser. A first fluid flow containing agents flows through a first fluid port positioned substantially centrally in the diffusion section and through the substrate in the chamber. A second fluid flow flows through a plurality of second fluid ports positioned circumferentially about the substrate in the chamber. The second fluid flow circumferentially surrounds the first fluid flow to direct the first fluid flow and any agents contained therein toward a central portion of the substrate.

In one embodiment, flow is reversed through the first fluid port to move any agents positioned on the central portion of the substrate out of the chamber in streamlines that flow through a central portion of the first fluid port. Flow through the plurality of second ports may be prevented when reversing flow through the first fluid port.

This invention is not limited in its application to the details of construction and the arrangement of components set forth in the preceding or proceeding description or illustrated in the drawings. The invention is capable of other embodiments and of being practiced or of being carried out in various ways. Also, the phraseology and terminology used herein is for the purpose of description and should not be regarded as limiting. The use of "including", "comprising", "having", "containing", "involving", and variations thereof herein, is meant to encompass the items listed thereafter and equivalents thereof as well as additional items.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 7 shows pulse field gel of elution fractions obtained following an operating protocol like that of Example 2.

DETAILED DESCRIPTION

Figure 1A:
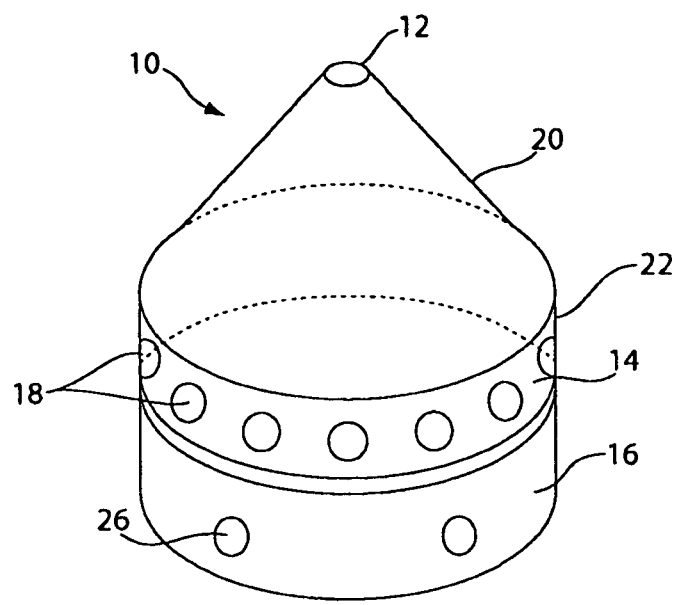
FIGS. 1a and 1b are views of a chamber, according to one embodiment of the invention.

The invention in based in part on the discovery of a chamber (referred to herein interchangeably as a "reaction chamber") that is able to isolate and/or manipulate large agents without loss of structural integrity. In the case of agents such as genomic DNA, the chamber is able to isolate and/or manipulate genomic DNA without shearing, thereby yielding genomic fragments that are at least tens or hundreds of kilobases in length, and more preferably megabases in length. These manipulations can be carried out on the order of hours rather than days, as is commonplace in the prior art. Moreover, the invention contemplates automated handling of the chamber (and the device comprising it). These features alone and more preferably in combination define an apparatus and method of use thereof that greatly enhances and facilitates analysis of large molecules such as but not limited to genomic DNA. The ability to manipulate long stretches of DNA, facilitates various analyses including but not limited to identification of the source of the genomic material (e.g., in pathogen analysis and screening).

The invention provides a fluidic chamber that is minimally comprised of an inlet port, a porous substrate that allows fluid but not the agents of interest to pass through, and at least one side port. Fluid flow is used to introduce, manipulate, separate, remove and/or harvest agents and/or other constituents from the chamber. The invention further provides devices or systems that comprise the fluidic chamber. The invention further provides methods for using the fluidic chamber, device and/or system to handle, isolate, purify, and/or manipulate large molecular weight agents such as but not limited to naturally and non-naturally occurring agents such as naturally or non-naturally occurring polymers including but not limited to nucleic acids, proteins, polysaccharides, and the like. Possible uses of the chamber include but are not limited to agent (e.g., polymer) harvest, isolation, purification, and manipulation such as nucleic acid hybridization, restriction endonuclease analysis of nucleic acids, amplification of nucleic acids (including whole genome amplification), labeling of nucleic acids using intercalators and/or sequence specific and/or sequence non specific probes, covalent or non-covalent modification of nucleic acids including but not limited to biotinylation of nucleic acids and optionally subsequent conjugation to streptavidin coated beads, and the like. One or more of these manipulations may be carried out in the chamber according to the invention. Those of ordinary skill in the art will readily envision a variety of uses of the fluidic chamber (and devices) provided herein.

The chamber may also be used for concentration of agents, mixing of reactants, buffer exchange, and/or removal of waste products and excess reagents. In the process of carrying out any of the manipulations described herein, therefore, the chamber may function by concentrating an agent (e.g., genomic DNA) in a particular region, by distributing agents evenly across the substrate or other porous surface of the chamber, by promoting a reaction between the agent(s) and one or more other substrates or reagents, by separating agent(s) from other components present in the chamber including for example reaction catalysts, substrates and/or by products. The device is able to perform these various functions primarily by modulating the fluid flow and path into and out of the chamber as described in greater detail herein.

Fluid flow that is introduced through a central port and diffuser of the chamber may be substantially opposed to the substrate, according to some embodiments, such that the fluid flow is directed toward the substrate, unlike in field flow fractionation devices, where the flow is directed along a membrane. Any agents or other constituents in the fluid flow may be retained, at least temporarily, for manipulation on the substrate.

As used herein, the term 'agent' is used to refer to the molecule or compound being harvested, isolated, purified and/or manipulated within the chamber. As stated above, the agent may be naturally occurring or non-naturally occurring. It may be a cell that is lysed in the chamber in order to release cellular components such as but not limited to genomic DNA. It may be another vehicle that carries genetic material such as but not limited to a phage or virus. It may be a polymer such as but not limited to nucleic acids (including DNA, RNA, and the like), proteins (including peptides and polypeptides), polysaccharides, and the like. These agents may be introduced into the chamber directly or they may be provided to the chamber following manipulation of another agent such as but not limited to the cells that are lysed within the chamber to release nucleic acids.

In some embodiments, the chamber functions to separate agents from 'other constituents' (or other components) within the chamber. As used herein, the term 'other constituents' is used to refer to any component being physically separated from agents in the chamber. Other constituents may include reagents, waste material, and/or any material introduced to the chamber to act upon an agent and/or to alter the environment of the chamber. By way of example, other constituents may comprise lytic enzymes that are introduced into the chamber to lyse cells, cellular debris that is created following cell lysis, excess unbound probes, excess unbound intercalator, excess unincorporated nucleotides, restriction endonucleases, and the like.

Use of the chamber of the invention allows the structural integrity of agents to be maintained. This is particularly useful if the agent is otherwise fragile and subject to shearing or cleavage using conventional manipulation techniques. In one example, the reaction chamber may obviate the need to manually handle strands of DNA, which would otherwise result in the fragmentation of the DNA. In another manner, shear forces associated with velocity gradients in moving fluids of the reaction chamber may be controlled, such that longer strands of polymers, like genomic DNA, may remain intact within the reaction chamber. According to some embodiments, nucleic acids that are at least 30 kilobases, at least 40 kilobases, at least 50 kilobases, at least 100 kilobases, at least 150 kilobases, at least 500 kilobases, at least 1 megabase, or at least 5 megabases may be retained in the chamber intact for subsequent analysis.

The chamber may allow the processes described herein, and others, to be performed without or with minimal manual intervention by an operator, such as is typically required in other processes, like in those that involve agarose plugs. An automated process is one that requires initial input from an operator but thereafter occurs independent of operator intervention. Examples of automated processes or methods include the harvest of agents upon manual loading of a sample into the chamber or an apparatus comprising the chamber. It would preferably not require manual loading of fluid and/or reagents. It would also not preferably require manual elution of the agent from the chamber. The degree of automation desired and implemented will depend on the particular application and can be modified accordingly by one of ordinary skill in the art.

Accordingly, embodiments of the chamber may also be used with automated operating protocols, such that systems using the chamber may be operated with minimal or no operator involvement and/or oversight. One or more reaction chambers may be incorporated into a system that receives a sample, either manually or automatically, and then initiates an automated operating protocol for processing the sample that is carried out by a controller of the system. By way of example, one automated operating protocol may involve nucleic acid harvest, isolation and restriction digestion, as discussed herein. It will be understood by those of ordinary skill in the art that other protocols may also be automated and the invention is not to be limited in this regard.

The chamber is able to prepare samples for analysis in less time than is required by conventional techniques. Most if not all manipulations may be performed on the order of hours including less than 12 hours, preferably less than 9 hours, more preferably less than 6 hours and even more preferably less than 3 hours, depending on the embodiment. In still other embodiments, the manipulations may be carried out in less than 1 hour. As non-limited examples of the speed of manipulation and analysis according to the invention, cell lysis and labeling of released nucleic acids (e.g., by sequence specific probes and/or intercalators) may be performed in 6 hours or less (including 5.5 hours or less, 5 hours or less, 4.5 hours or less, 4 hours or less, 3.5 hours or less, 3 hours or less, 2.5 hours or less, 2 hours or less, or 1.5 hours or less), cell lysis and digestion of released nucleic acids may be performed in 4 hours or less (including 3.5 hours or less, 3 hours or less, 2.5 hours or less, 2 hours or less, 1.5 hours or less, or 1 hour or less).

As used herein, "harvesting" refers to the process of extracting an agent from a sample or from a component within a sample such as but not limited to a cell or phage. Harvesting may also refer to the extraction of a smaller nucleic acid from a larger nucleic acid, including for example extracting a nucleic acid from a chromosome whether the chromosome is naturally or non-naturally occurring.

As used herein, "isolating" refers to the process of separating the agent from other components or constituents in the sample and/or chamber. An example of an isolated agent is a nucleic acid that has been separated from the cell from which it was originally presented. As used herein, "purification" refers to the degree to which the agent is separated from other components or constituents in the sample and/or chamber. The more purified the agent, the fewer components or constituents it is still present with. As used herein, "manipulating" or "modifying" an agent are used interchangeably to refer to making a change to the agent including but not to limited binding a probe to the agent, deliberating cleaving the agent, and the like.

In some aspects of the invention, a number of processes are performed in the chamber. In the case of agents that are nucleic acids (including but not limited to genomic DNA), these processes may be harvest, isolation and/or purification of the nucleic acid (e.g., from a cell or from a sample including for example release of nucleic acids after chemical or enzymatic lysis (e.g., lysozyme and/or proteinase K digestion) of cells), digestion of the nucleic acid (e.g., using exonucleases or endonucleases), hybridization of sequence specific probes to the nucleic acids, and optionally binding of an intercalator to the nucleic acids.

The chamber and system of the invention allow these processes to occur rapidly, particularly as compared to prior art methods. For example, lysis of cells through to the digestion of nucleic acids can occur in about 2.5 hours or less, lysis of cells through to hybridization with probes can occur in about 3.5 hours or less, and lysis of cells through to intercalation can occur in about 4 hours or less.

The rapid harvest and/or manipulation of agents such as nucleic acids is due at least in part to the ability of the chamber and the system to sufficiently expose agents (including cells and nucleic acids) to the various reagents (including enzymes, co-factors, buffers, probes, intercalators, quenchers, and the like) introduced into the chamber. The fluid flow through the chamber facilitates in some embodiment relatively uniform distribution of agents and reagents onto the substrate (e.g., the membrane). This ensures better mixing of reaction components within the chamber and less shearing forces than are provided by prior art methods.

The following is an exemplary and non-limiting example of the use and operation of the chamber. A test sample (e.g., a sample suspected of containing a biowarfare agent such as an anthrax spore) is introduced into the chamber through the introduction port. The reservoir port is open while the side port(s) is closed. Temperature of the chamber may be room temperature (e.g., about 25 C.). Leaving the configuration of the chamber as is, a solution of lysozyme and proteinase K is introduced into the chamber followed by an incubation at about 60 C. This is followed by removal of cell debris by flowing (wash) fluid into the introduction port and out through the side port(s). The side port(s) is again closed and a solution comprising restriction enzyme is introduced into the chamber through the introduction port followed by incubation at about 40 C. Restriction enzyme is then removed, along with other small molecular weight debris and reagents through the side port(s), and then the digested DNA fragments are eluted from the chamber through the side port(s). The fragments may then be analyzed in any number of ways including but not limited to gel electrophoresis to determine the distribution of fragments resulting from digestion with that particular enzyme. Unique and thus identifying fragment distributions will be used to identify the presence of particular agents such as anthrax spores. These patterns in most instances will be known a priori and the analysis will require a comparison with that known pattern and distribution.

Using the methods of the invention, it has been possible to extract restriction fragments corresponding to 340 microns in length, as well as fragments corresponding to more than 291 kilobases, about 210 kilobases, about 194 kilobases, about 145 kilobases, and about 60 kilobases from *Bacillus* spores using the chamber of the invention. These were prepared by the chamber in about 4 hours, using an automated process. This is to be compared to the prior art methodology that takes about 6 days and results in less clearly discernable restriction fragments. In this way, the chamber and system can be used to rapidly identify pathogens, leading to more rapid response times by emergency personnel.

The chamber and method of the invention has also been used to successfully harvest nucleic acids on the order of 1700 microns in length. It is to be understood that the quality of the nucleic acids prepared using the chamber and methods of the invention is similar if not superior to the quality achieved using gel plug methods of the prior art. Moreover, the methods of the invention are far faster than those prior art methods. Another advantage of the methods of the invention are that the nucleic acids prepared according to the methods provided herein are not random fragments. This is so at least because of the ability of the invention to maintain the nucleic acid in an intact form (i.e., without substantial shearing or unintentional fragmentation or cleavage). Nucleic acid recoveries range from at least 50% of input to greater than 75% of input. In some embodiments, greater than 80%, greater than 85%, greater than 90%, and in some embodiments about 100% of input is recovered.

Still other applications contemplated by the invention are hybridization of genomic DNA with fluorescently labeled probes (e.g., to characterize sequence specificity and site occupancy of DNA binding ligands), fluorescently labeled restriction enzyme labeling of genomic DNA (e.g., for rapid mapping of large DNA), detection and optionally quantification of nucleic acids and/or proteins utilizing DNA as a capture unit carrier, plasmid preparations from bacterial cells and/or cultures, combined DNA isolation and amplification, and the like.

It is to be understood that similar methods can be employed to identify and analyze nucleic acids from subjects (e.g., for genomic sequencing, for forensic analysis, for paternity testing, etc.). Many of these analyses can be accomplished using restriction enzymes akin to the analysis performed with respect to pathogen detection and identification (as described above). As an example, restriction fragment length polymorphism analysis (wherein differences in length of restriction fragments can be used to determine the source of a nucleic acid) can be facilitated by harvesting and manipulating nucleic acids in the chamber.

Similarly, samples can be analyzed for the presence (or absence) of proteins as may be applicable to diagnostic, prognostic or therapeutic monitoring. In some embodiments, proteins may be detected and/or identified by binding them to binding partners (or probes) such as antibodies or antibody fragments. Following labeling within the chamber, the proteins may be eluted (as described herein) and analyzed by any number of systems and instruments including but not limited to FACS or other single molecule detection systems. The chamber and system may also be used to simply harvest and separate proteins in a sample away from debris in the sample, thereby allowing the protein profile of a sample to be analyzed using for example standard techniques such as Western blots, HPLC, mass spectrometry, and the like.

Figure 1B:
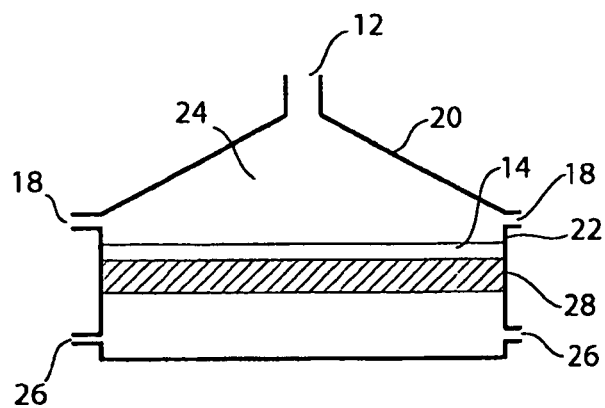

The chamber 10 minimally comprises an central port 12, a porous substrate 14 that allows fluid but not the agents of interest to pass through, a reservoir 16 below the substrate, and at least one side port 18. FIGS. 1*a* and 1*b*, which show a schematic view and a cross-sectional view of a chamber, according to one embodiment of the invention. As illustrated, the chamber comprises a diffuser 20, a body section 22, and a porous substrate 14 that lies within the body section. A flow region 24 lies between the diffuser 20 and a first side of the substrate, and a reservoir lies on an opposite side of the substrate. A central port 12 (alternately referred to herein as a fluid introduction port, an inlet port, or injection port) is positioned substantially centrally in the diffuser 20 and may be used to move fluids into and/or out of the flow region of the chamber. One or more side ports 18 (alternately referred to herein as fluid exit ports) are positioned about the flow region, and near the first side of the substrate. The one or more side ports may be used to direct flow, typically introduced through the central port, in different directions. Waste ports 26 (alternately referred to herein as reservoir ports) provide fluid access to the reservoir 16 and may be used to introduce and/or remove fluids therefrom.

Embodiments of the chamber may be constructed with different configurations and dimensions, some examples of which are discussed herein. By way of example, the diffuser provides a diffusive flow pathway between the central port and the flow region, which, in many embodiments, may laterally spread the flow of fluid introduced through the central port to promote even distribution of agents about the substrate.

The diffuser may be shaped differently according to various embodiments. The diffuser is typically designed to smoothly widen or diffuse flow that enters the flow region from the central port without subjecting agents to excessive shear forces. As shown in FIGS. 1*a* and 1*b*, the diffuser may be shaped like a symmetric, truncated cone with substantially linear sides that form an angle of about 60 degrees with a line that extends along a central axis of the central port. It is to be appreciated, however, that the diffuser may include walls that are angled differently, or that are gently curved instead of being linear, as aspects of the invention are not limited in this regard. According to some embodiments, the diffuser may include flat sides, appearing more like a truncated pyramid. Other embodiments may also include asymmetric diffusers.

Various fluidic modeling techniques, such as flow testing with dyes and/or computational fluidic modeling may be used to optimize the diffuser shape for various operating conditions and/or to promote the even distribution of agents about the substrate that have been introduced through the central port. Similar techniques may be used to optimize the diffuser for the minimization of shear forces that occur in the flow region or to accomplish other effects.

The central port is typically positioned in the central portion of the diffuser and, as shown in FIGS. 1a and 1b, is configured to direct a flow of fluid orthogonally toward the substrate of the chamber. According to other embodiments, however, the central port may be offset to one side of the diffuser, and in this respect, the term 'central' as used to describe the central port should not be found to be limiting. Additionally or alternately, the central port may direct fluid flow toward the substrate at an angle, instead of orthogonally. It is also to be appreciated that embodiments of the chamber may include a plurality of central ports positioned about the diffuser, and in this respect, the term 'central port' should not be construed to refer solely a single fluid port.

The diffuser and/or central port, when described as being substantially opposed to the substrate, are understood to be positioned to direct fluid to impinge on a surface of the substrate. That is, at least a portion of the fluid flow is directed to intersect with the substrate.

The porous substrate (also referred to herein as a membrane or a filter) is typically positioned to receive flow that is introduced to the chamber from the central port, as shown in the embodiment of FIGS. 1a and 1b, such that agents in flow passing therethrough may be received on the substrate. The substrate typically has a threshold size that relates to the porosity of the substrate and that describes the size of agents or other constituents that are prevented from passing therethrough. According to some embodiments, the substrate has a threshold size that prevents the passage of cells, of genomic DNA, of proteins, and the like, although other threshold sizes are possible, as aspects of the invention are not limited in this respect.

The substrate may comprise circular shaped, removable filter material that is supported on a porous frit 28 in the chamber, as shown in FIGS. 1a and 1b. Some operating protocols may utilize substrates with different threshold sizes, or that are constructed differently, and may benefit from being removable form the chamber. The substrate of some embodiments may be sandwiched between a frit on the reservoir side and a supporting structure on the flow region side, such that the substrate is supported when/if flow is introduced from the reservoir to the flow region of the chamber, such as during elution. According to some embodiments, the substrate itself is relatively stiff, such that a frit or other supporting structure may not be required.

Embodiments of the chamber may include a body section that defines a wall of the chamber that lies between the substrate and the diffuser. As shown in FIGS. 1a and 1b, the body section is substantially cylindrical in shape and extends for a relatively short distance between the diffuser and the substrate. In other embodiment, the diffuser may be shaped differently, or the diffuser may extend directly to the substrate, such that there is no body section at all in the chamber.

One or more side ports are positioned about the flow region, generally adjacent to the substrate, as shown in FIGS. 1a and 1b, where the side ports are positioned about the circumference of the body section, or circumferentially. The one or more side ports, generally speaking, are positioned to allow fluid to flow in the flow region, above the substrate without also passing through the substrate. In many embodiments, side port(s) are positioned to allow portions of fluid that are introduced toward a central portion of the substrate (such as from the central port) to move radially outward to flow substantially laterally across the top surface of the substrate.

Figure 2:
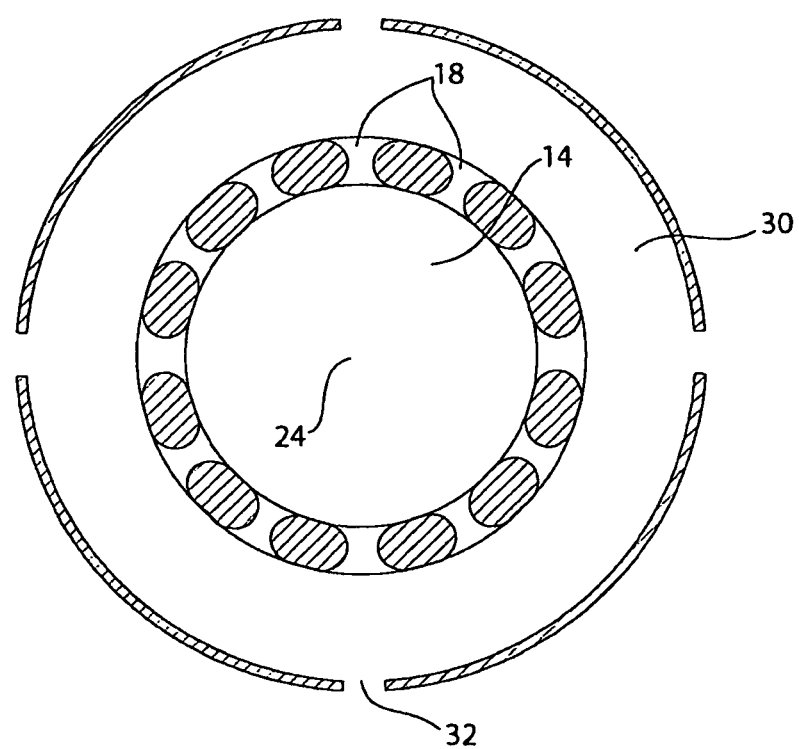
FIG. 2 shows a cross sectional view of an embodiment of a chamber that illustrates the construction and placement of side ports, according to one embodiment.

Embodiments of the chamber may have multiple side ports, and in some embodiments have 2 side or 4 side ports positioned at even intervals about the chamber, such as on the body section. It is to be appreciated that embodiments of the chamber may have any number of side ports, such as 8 side ports, 11 side ports, or 16 side ports positioned evenly about the chamber, as illustrated in FIG. 2, or even a continuous slot or plenum that defines a substantially continuous side port extending partially or continuously about the flow region of the chamber. The one or more side ports are typically positioned so that fluid flow, initially directed toward the substrate, may change direction, such that at least a portion of the fluid flow moves toward a direction that is substantially parallel to the surface of the substrate facing the flow region. In many embodiments, side port(s) are positioned so that portions of fluid flow, initially directed toward the substrate, may be urged to move toward side ports positioned about the perimeter of the body section of the chamber, and thus move laterally over a surface of the substrate that faces into the chamber.

Construction and placement of the side ports may be guided by flow testing and/or computational analysis to minimize any low flow or dead zones in the flow region, reduce shear that might be imparted to agents, and/or to promote favorable velocity gradients through the flow region, such as during separation modes.

Figure 3:
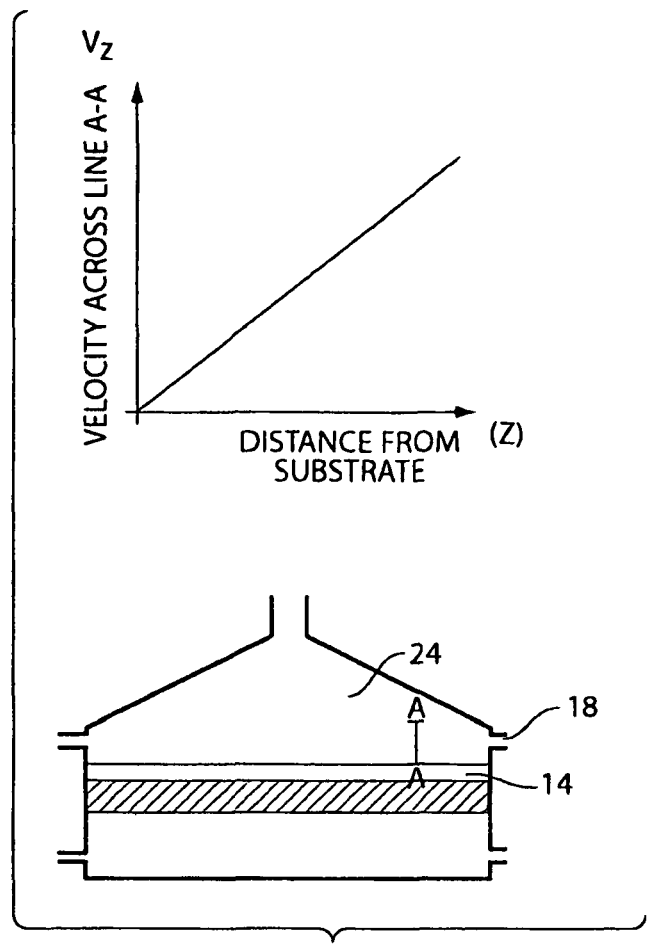
FIG. 3 shows a velocity profile, according to one embodiment, near a side port of a chamber during a separation mode.

FIG. 2 shows a cross-sectional top view of one embodiment of a chamber taken laterally across and cutting through the side ports 18. As shown, each of the side ports have a smooth, curved opening to the flow region. Such a design may help minimize or eliminate any eddies, reduced flow, or dead regions that might otherwise be present in the flow region when operated in a separation mode. Reducing or eliminating such dead zones can promote more efficient separation of agents from non-agents, during separation modes, or more even distribution of agents during press down modes, among other benefits.

FIG. 2 also shows a cavity 30 that may be incorporated into embodiments of the chamber to promote more equal flow through each of the side ports. The cavity, as shown, is in fluid communication with four ports 32 that are connected to an external pump or valve that controls the proportion of flow that passes though the side ports. Any vacuum (or positive pressure) produced by the external pump, in turn, causes a vacuum (or pressure) in the flow equalization cavity. The cavity allows the vacuum (or pressure) to equalize across each of the side ports, and thus promotes even flow rates through each of the side ports. It is to be appreciated that the flow equalization zone may help accomplish a substantially symmetric fluid flow through the flow region (about an axis that lies along the central port), which may promote more efficient operation of the chamber. It is also to be appreciated that the cavity is but one example of features that may be used to equalize flow across multiple side ports, and that other methods and features for tuning flow may also be employed.

Embodiments of the chamber, and particularly those portions that are in contact with the flow region, like the central port, the diffuser, the side ports, the body section, and the substrate, may be designed to promote particular flow conditions. For instance, according to some embodiments, the chamber may be constructed to promote laminar flow so that shear forces acting on agents therein may be minimized. Additionally or alternately, the chamber may be constructed to promote flow through the side ports with a velocity profile, as shown in FIG. 3, where flow near the substrate is slower than flow that is further from the substrate. Such velocity profiles may prove advantageous during separation modes of the chamber, as discussed in greater detail herein.

As shown in FIG. 1*a*, the overall shape of the chamber may be cylindrical with a cone shaped diffuser. However, it is to be appreciated that embodiments of the chamber may be shaped differently as well, including oblong or ovalized shapes, or even shapes that include angular sides, like chambers that are square or rectangular in cross section.

Figure 4:
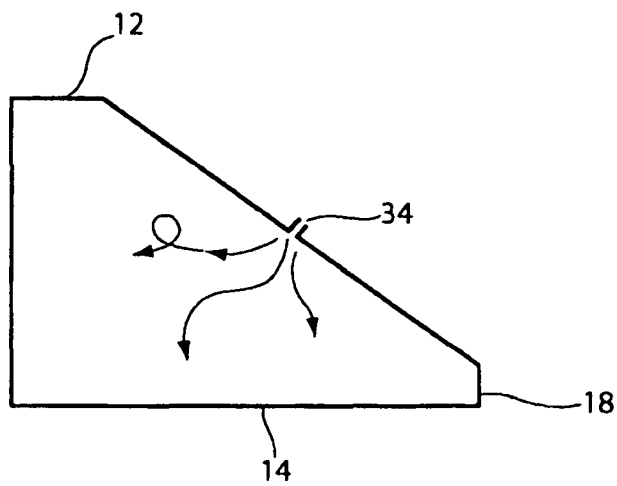
FIG. 4 shows an embodiment of a chamber that includes jets that may be used to agitate contents of the chamber.

Embodiments of the chamber may have features to promote mixing, such as microscale jets 34 that create a stirring motion to agitate reactants that are spread on or about the substrate. Microscale jets may be issued from small holes, such as micron sized holes, in the diffuser, according to one embodiment illustrated in FIG. 4. The jets may carry a relatively large momentum even at low flow rates and may agitate the agents spread on the substrate without substantial loss of the agents through side ports.

Embodiments of the chamber may also be equipped with features to regulate temperature in the flow region. According to one embodiment, a frit that lies below and supports the substrate is made of a thermally conductive material, like stainless steel, and may be heated or cooled by an external source, like a thermoelectric module, to regulate temperature. Additionally or alternately, fluid may pass through the reservoir to cool or heat the reservoir side of the substrate/frit to rapidly cool or heat the chamber. The chamber may also be equipped with other devices, like a radiant heater that heats fluid in the chamber through non-contact methods, or like an inline heater that heats fluids entering the chamber which, in turn, may help maintain uniform temperature conditions throughout the chamber volume.

As described herein, a reservoir may be positioned on a side of the substrate opposite to the flow region, as shown in FIGS. 1*a* and 1*b*. Broadly speaking, the reservoir receives fluid that has passed through the substrate from the flow region prior to the fluid being evacuated from the chamber through one or more waste ports. It is however to be appreciated that the reservoir may be used to accomplish other effects, such as heating and/or cooling of the flow region, as discussed herein. Additionally, some embodiments may not include a reservoir, but instead, directly pass fluids passing through the substrate to an outflow tube.

Modes of Operation

The chamber may be operated in several different modes, including a press-down mode, a separation mode, an elution mode, a reacting mode, and a focusing mode, among others. Each of these modes are illustrated schematically in FIGS. 5*a*-5*f*.

Figure 5A:
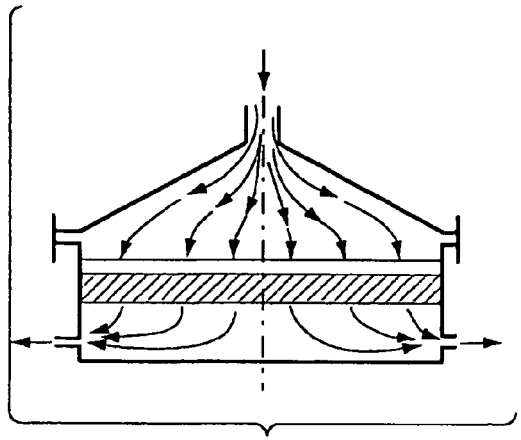
FIGS. 5a-5f show, schematically, an embodiment of the chamber in various modes of operation.

The chamber may be operated in a press down mode (also referred to herein as an injection mode) to position agents or other constituents near the substrate or simply to introduce agents to the flow region where they may be acted upon. The agents or other constituents introduced during a press down mode may have been present in the flow region at the beginning of the mode, or may be introduced to the chamber through the central port during the press down mode. In a press down mode, as shown in FIG. 5*a*, fluid that may contain agents is introduced into the flow region from the central port. The fluid passes through the flow region, the substrate, the reservoir, and then exits the chamber through the waste ports. Any agents or other constituents present in the fluid that are larger than a threshold size of the substrate will be retained in flow region, and "pressed down" or held against the substrate. There is typically no flow through the side ports during a press down mode, to prevent the fluid and any agents therein from exiting the flow region, although, according to some embodiments, some flow through the side ports may be acceptable.

Figure 5B:
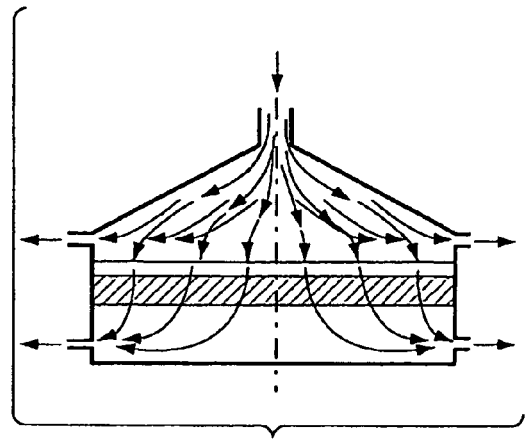

A separation mode may be used to separate agents and other constituents that reside within the flow-region. As shown in FIG. 5*b*, fluid is introduced to the chamber from the central port, and a first portion of the fluid flows through the flow region and the substrate, and then exits the chamber through the reservoir/waste ports. A second portion of the fluid flow enters the flow region from the central port and then exits the flow region through the plurality of side ports that are positioned on opposed sides of the chamber. Broadly speaking, the first portion of the fluid flow urges agents and/or other constituents hydro dynamically toward the substrate. The other constituents or agents that migrate away from the substrate and into the flow region, such as through diffusion, are urged through the side ports and out of the chamber by the second portion of the fluid flow. The combination of the first and second portions of fluid flow allow the other constituents to be separated from agents within the chamber.

Embodiments of the chamber allow separation of agents from other constituents primarily as a result of two factors. First, flow through the substrate may create a concentration of agents and other constituents at the substrate. For larger components, typically the agents, the concentration gradient may decrease more rapidly at points further from the substrate. Second, diffusion of components (agents or other constituents) away from the substrate occurs and may be driven by the concentration gradient within the chamber. Smaller components (often the other constituents) typically have concentration gradients that decrease less rapidly, meaning essentially that portions further from the substrate will be more greatly populated by other constituents than agents (taken as percentages of the total amounts of other constituents and agents, respectively), since the other constituents typically have greater diffusion rates than the agents. These factors, as illustrated in FIG. 3, allow the chamber to be used in a separation mode to remove other constituents from the chamber that have concentration distributions extending away from the substrate. Due to their faster diffusion rates, smaller components (typically the other constituents) tend to quickly reestablish the concentration gradient and repopulate the layers of liquid further from the substrate that have exited the chamber through side ports. Thus, allowing the other constituents to be efficiently removed from the chamber, while slowly diffusing larger components (typically the agents) may be retained on or about the substrate. Similarly, the buffer in the chamber can be exchanged efficiently using the separation mode (also referred to herein as selective retention).

The flow of fluid toward the side ports may have greater velocity at points that are further from the substrate, as shown in FIG. 3, due to boundary layer effects of the fluid flow near the substrate. The flow may be linearly approximated in the region above the substrate, as is also represented in FIG. 3. As discussed herein, this phenomenon may aid with the removal of smaller components from the reaction chamber, whose distribution about the membrane extends further from the membrane than the distribution of large particles, and thus into the flow that is moving radially toward the side ports, or at least that is moving radially toward the side ports with a greater velocity.

Figure 5C:
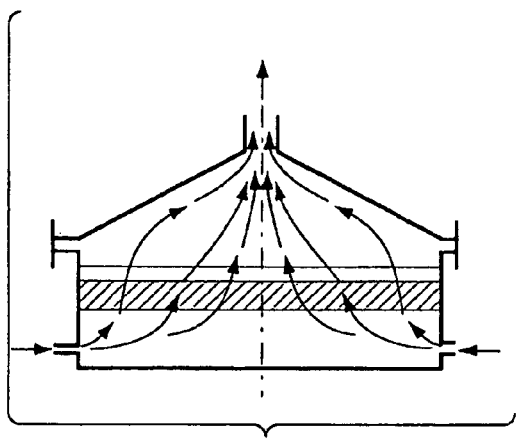

Embodiments of the chamber utilize other devices to urge agents and/or constituents about a chamber. By way of example, electric fields, and/or magnetic fields may be used in combination with or in place of the flow fields and diffusion mechanisms discussed herein.

During an elution mode, the contents of the flow region, including any agents therein, exit the chamber through one or more of the central port and/or side ports. According to one embodiment, as shown in FIG. 5c, fluid is introduced to the chamber through each of the waste ports and urges any agents or non-agents in the flow region out of the chamber through the central port. In this embodiment, the side ports may be closed to prevent fluid from passing there. It is to be appreciated, however, that elution may take place through other approaches, such as by introducing fluid to the flow region through a first portion of the side ports and out of the flow region through a second portion of side ports, or through other schemes. Additionally or alternately, elution may be performed electrokinetically by creating an electric field that directs agents out of the flow region through the central and/or side ports.

Figure 5D:
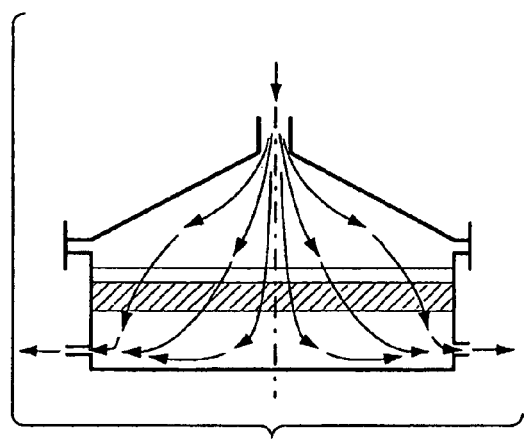

Reactions are allowed to occur in the flow region of the chamber during a reaction mode. According to some embodiments, reaction modes may occur while fluid is flowing into the flow region from the central port and out of the flow region through the substrate, as shown in FIG. 5d. Here, the fluid flow may concentrate reactants about the substrate within the chamber to effectively create a localized, reaction zone within the chamber for agents and other constituents, like reagents that are introduced to the flow region. Such reagents may be introduced while agents, previously introduced to the chamber, are being held at the substrate. Alternately, reagents may be introduced to the chamber with agents in a common fluid flow. Alternately, fluid flow through the reaction may be halted altogether during a reaction mode, which may allow greater diffusion of reactants throughout the flow region.

Reaction modes may also involve controlling the environment of the flow region to promote reactions, such as by controlling the temperature, light conditions, and the like.

Figure 5E:
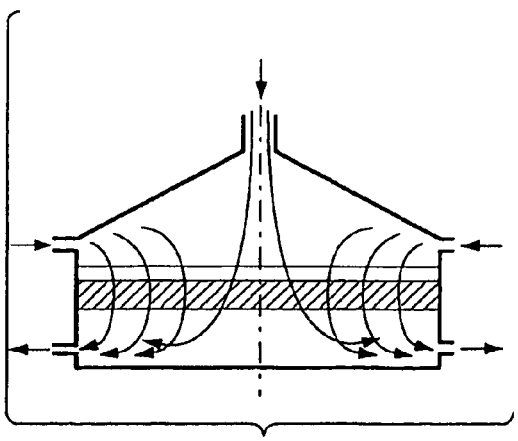

The chamber may be operated in a focusing mode to position agents on a select portion of the substrate, such as a central portion. As shown in FIG. 5e, a first fluid that includes agents is introduced to the flow region through the central port while a second fluid is also introduced to the flow region through the side ports. The second fluid flow circumferentially surrounds the first fluid as both the first and second fluids pass through the substrate into the reservoir. Agents in the first fluid are held at a central portion of the substrate through which the first fluid passes—and in this regard, are focused to the central portion of the substrate. It is to be appreciated that similar methods may be used to position agents on portions of the substrate other than the central portion, as aspects of the invention are not limited in this respect.

Figure 5F:
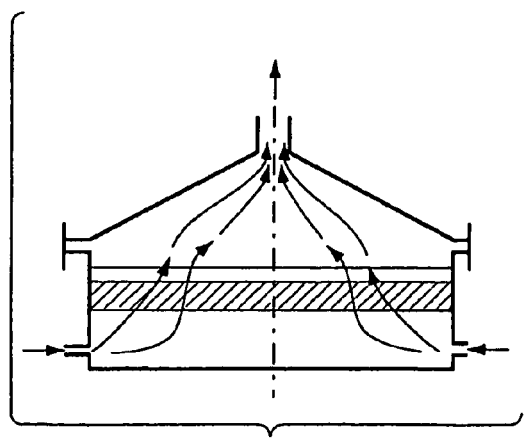

The chamber may also be used, in a focusing mode, to position agents in particular streamlines of fluid that exits the chamber, such as central streamlines. Fluid may be moved through the substrate from the reservoir to lift agents off of the substrate and out of the chamber through the central port, as shown in FIG. 5f. When agents are only present on central portions of the substrate, the flow that exits the central port will only include agents in its central streamlines. Flow through the side ports may be prevented during such focusing modes. Alternately, some flow may be introduced through the side ports to further direct the fluid that enters the flow region from through the substrate toward central portions of the flow exiting the chamber through the central port, as aspects of the invention are not limited in this respect.

Fluid flow may be controlled throughout the chamber during the various modes of operation with different configurations of pumps and valves. According to some embodiments, flow is controlled by a first variable flow rate pump in fluid communication with the central port and by a second variable flow rate pump that is in fluid communication with the side ports, and with a valve that is configured to control flow through the waste ports. It is to be appreciated, however, that other arrangements of pumps (either pressure or vacuum) and valves may be used to control flow thought the chamber in various modes of operation, as aspects of the invention are not limited in this respect. Additionally, aspects of the invention are not limited to any one type of pump or valve.

Embodiments of the chamber may be operated by a controller that receives information for a particular operating protocol and, in turn, controls pumps and/or valves to run the system automatically to complete the protocol. The term 'automatically', as used herein, refers to a system that is capable of switching between modes of operation without the intervention of an operator, such as between a press down mode, a separation mode, a reaction mode, and/or an elution mode, among others, or to a system that is otherwise capable of altering operating condition, such as flow rates or temperatures without manual operator intervention, such as by following an predefined operating protocol or by controlling the system to predetermined set points. The controller and operating protocol combination may be implemented in any of numerous ways. For example, in one embodiment the controller and operating protocol combination may be implemented using hardware, software or a combination thereof. When implemented in software, the software code can be executed on any suitable processor or collection of processors, whether provided in a single computer or distributed among multiple computers. It should be appreciated that any component or collection of components that perform the functions described herein can be generically considered as one or more controllers that control the functions discussed herein. The one or more controllers can be implemented in numerous ways, such as with dedicated hardware, or with general purpose hardware (e.g., one or more processors) that is programmed using microcode or software to perform the functions recited above. The one or more controllers may be included in one or more host computers, one or more storage systems, or any other type of computer that may include one or more storage devices coupled to the one or more controllers.

In this respect, it should be appreciated that one implementation of the embodiments of the present invention comprises at least one computer-readable medium (e.g., a computer memory, a floppy disk, a compact disk, a tape, etc.) encoded with an operating protocol in the form of a computer program (i.e., a plurality of instructions), which, when executed by the controller, performs the herein-discussed functions of the embodiments of the present invention. The computer-readable medium can be transportable such that the treatment protocol stored thereon can be loaded onto any computer system resource to implement the aspects of the present invention discussed herein. In addition, it should be appreciated that the reference to an operating protocol or controller which, when executed, performs the herein-discussed functions, is not limited to an application program running on a host computer. Rather, the term operating protocol is used herein in a generic sense to reference any type of computer code (e.g., software or microcode) that can be employed to program a processor to implement the herein-discussed aspects of the present invention.

The system may also comprise one or more sensors that receive information from the chamber or fluidic conduits used to connect the chamber to other portions of the system. Such sensors may receive information regarding pressure, temperature, flow rates, and the like, in any portion of the chamber or system. The system may also receive information from detectors that are used to analyze or detect the presence of an agent in a portion of the system.

The processing steps of the invention generally comprise the use of one or more reagents (i.e., at least one reagent) that acts on or reacts with and thereby modifies an agent. At least one reagent however is less than an infinite number of reagents as used herein and more commonly represents less than 1000, less than 100, less than 50, less than 20, less than 10, or less than 5 reagents. The nature of the reagents will vary depending on the processing step being performed with such reagent. The reagent may be a lysing agent (e.g., a detergent such as but not limited to deoxycholate), a labeling agent or probe (e.g., an intercalator or a sequence-specific probe), an enzyme (e.g., a lytic enzyme, an exonuclease, or an endonuclease such as a restriction endonuclease), an enzyme co-factor (e.g., cations such as $Mg^{2+}$, a stabilizer (e.g., an anti-oxidant), and the like. One of ordinary skill in the art can envision other reagents to be used in the invention. Although the agent can be modified through those techniques mentioned above, it is to be appreciated that other techniques can also be used to modify the agent.

Additionally, the fluids used in the invention may contain other components (or constituents) such as buffering compounds (e.g., TRIS), chelating compounds (e.g., EDTA), ions (e.g., monovalent, divalent or trivalent cations or anions), salts, preservatives, and the like.

By way of example, a fluid may contain a lysing agent that lyses agents (e.g., eukaryotic cells or pathogens such as bacteria, viruses and the like) in the chamber, thereby releasing cellular contents, such as nucleic acids, into the chamber.

The invention is not limited in the nature of the agent being harvested, manipulated, detected or analyzed (i.e., the target agent). These agents include but are not limited to cells and cell components (e.g., proteins and nucleic acids), chemicals and the like. These agents may be biohazardous agents as described in greater detail herein. Target agents may be naturally occurring or non-naturally occurring, including agents synthesized ex vivo but released into a natural environment. As described herein, the methods and systems of the invention can be used to modify one or more agents concurrently, simultaneously or consecutively. A plurality of agents is more than one and less than an infinite number. It includes less than $10^{10}$, less than $10^9$, less than $10^8$, less than $10^9$, less than $10^7$, less than $10^6$, less than $10^5$, less than $10^4$, less than 5000, less than 1000, less than 500, less 100, less than 50, less than 25, less than 10, or less than 5 agents, or as little as one agent, as well as every integer therebetween as if explicitly recited herein.

The conditions, temperature, buffers and reagents of the chamber will vary depending on the particular type of modification being performed and will be known to those of ordinary skill in the art. See for example Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981).

The invention can be applied to the detection and optionally identification and/or quantification of any agent, including rare agents or agents that would be costly to detect given the reagents necessary therefor. One example of such agents is biohazardous or biowarfare agents. These agents can be biological or chemical in nature. Biological biowarfare agents can be classified broadly as pathogens (including spores thereof) or toxins. As used herein, a pathogen (including a spore thereof) is an agent capable of entering a subject such as a human and infecting that subject. Examples of pathogens include infectious agents such as bacteria, viruses, fungi, parasites, mycobacteria and the like. Prions may also be considered pathogens to the extent they are thought to be the transmitting agent for CJD and like diseases. As used herein, a toxin is a pathogen-derived agent that causes disease and often death in a subject without also causing an infection. It derives from pathogens and so may be harvested therefrom. Alternatively, it may be synthesized separately from its naturally occurring source. Biological warfare agents may be weaponized (i.e., aerosolized) for maximum spread. Examples of pathogens are provided below.

CDC Category A agents include *Bacillus anthracis* (otherwise known as anthrax), *Clostridium botulinum* and its toxin (causative agent for botulism), *Yersinia pestis* (causative agent for the plague), variola major (causative agent for small pox), *Francisella tularensis* (causative agent for tularemia), and viral hemorrhagic fever causing agents such as filoviruses Ebola and Marburg and arenaviruses such as Lassa, Machupo and Junin.

CDC Category B agents include Brucellosis (*Brucella* species), epsilon toxin of *Clostridium perfringens*, food safety threats such as *Salmonella* species, *E. coli* and *Shigella*, Glanders (*Burkholderia mallei*), Melioidosis (*Burkholderia pseudomallei*), Psittacosis (*Chlamydia psittaci*), Q fever (*Coxiella burnetii*), ricin toxin (from *Ricinus communis*—castor beans), Staphylococcal enterotoxin B, Typhus fever (*Rickettsia prowazekii*), viral encephalitis (alphaviruses, e.g., Venezuelan equine encephalitis, eastern equine encephalitis, western equine encephalitis), and water safety threats such as e.g., *Vibrio cholerae, Cryptosporidium parvum*.

CDC Category C agents include emerging infectious diseases such as Nipah virus and hantavirus.

Further examples of bacteria that can be harvested and/or manipulated according to the invention include Gonorrhea, *Staphylococcus* spp., *Streptococcus* spp. such as *Streptococcus pneumoniae*, Syphilis, *Pseudomonas* spp., *Clostridium difficile, Legionella* spp., *Pneumococcus* spp., *Haemophilus* spp. (e.g., *Haemophilus influenzae*), *Klebsiella* spp., *Enterobacter* spp., *Citrobacter* spp., *Neisseria* spp. (e.g., *N. meningitidis, N. gonorrhoeae*), *Shigella* spp., *Salmonella* spp., *Listeria* spp. (e.g., *L. monocytogenes*), *Pasteurella* spp. (e.g., *Pasteurella multocida*), *Streptobacillus* spp., *Spirillum* spp., *Treponema* spp. (e.g., *Treponema pallidum*), *Actinomyces* spp. (e.g., *Actinomyces israelii*), *Borrelia* spp., *Corynebacterium* spp., *Nocardia* spp., *Gardnerella* spp. (e.g., *Gardnerella vaginalis*), *Campylobacter* spp., *Spirochaeta* spp., *Proteus* spp., and *Bacteriodes* spp.

Further examples of viruses that can be harvested and/or manipulated according to the invention include Hepatitis virus A, B and C, West Nile virus, poliovirus, rhinovirus, HIV, Herpes simplex virus 1 and 2 (including encephalitis, neonatal and genital forms), human papilloma virus, cytomegalovirus, Epstein Barr virus, Hepatitis virus A, B and C, rotavirus, norovirus, adenovirus, influenza virus including influenza A virus, respiratory syncytial virus, varicella-zoster virus, small pox, monkey pox and SARS virus.

Further examples of fungi that can be harvested and/or manipulated according to the invention include candidiasis, ringworm, histoplasmosis, blastomycosis, paracoccidioidomycosis, crytococcosis, aspergillosis, chromomycosis, mycetoma, pseudallescheriasis, and tinea versicolor.

Further examples of parasites that can be harvested and/or manipulated according to the invention include both protozoa and nematodes such as amebiasis, *Trypanosoma cruzi*, Fascioliasis (e.g., *Facioloa hepatica*), Leishmaniasis, *Plasmodium* (e.g., *P. falciparum, P. knowlesi, P. malariae,*) Onchocerciasis, Paragonimiasis, *Trypanosoma brucei*, Pneumocystis (e.g., Pneumocystis carinii), *Trichomonas vaginalis*, Taenia, *Hymenolepsis* (e.g., *Hymenolepsis nana*), Echinococcus, Schistosomiasis (e.g., *Schistosoma mansoni*), neurocysticercosis, *Necator americanus*, and *Trichuris trichuria*, Giardia.

Further examples of mycobacteria that can be harvested and/or manipulated according to the invention include *M. tuberculosis* or *M. leprae*.

Examples of toxins include abrin, ricin and strychnine. Further examples of toxins include toxins produced by *Corynebacterium diphtheriae* (diphtheria), *Bordetella pertussis* (whooping cough), *Vibrio cholerae* (cholera), *Bacillus anthracis* (anthrax), *Clostridium botulinum* (botulism), *Clostridium tetani* (tetanus), and enterohemorrhagic *Escherichia coli* (bloody diarrhea and hemolytic uremic syndrome), *Staphylococcus aureus* alpha toxin, Shiga toxin (ST), cytotoxic necrotizing factor type 1 (CNF1), *E. coli* heat-stable toxin (ST), botulinum, tetanus neurotoxins, *S. aureus* toxic shock syndrome toxin (TSST), Aeromonas hydrophila aerolysin, *Clostridium perfringens* perfringolysin O, *E. coli* hemolysin, *Listeria monocytogenes* listeriolysin O, *Streptococcus pneumoniae* pneumolysin, *Streptococcus pyogenes* streptolysine O, *Pseudomonas aeruginosa* exotoxin A, *E. coli* DNF, *E. coli* LT, *E. coli* CLDT, *E. coli* EAST, *Bacillus anthracis* edema factor, *Bordetella pertussis* dermonecrotic toxin, *Clostridium botulinum* C2 toxin, *C. botulinum* C3 toxin, *Clostridium difficile* toxin A, and *C. difficile* toxin B.

The foregoing lists of infections are not intended to be exhaustive but rather exemplary.

It may be necessary, in some embodiments, to disrupt pathogen cell walls, cell membranes or viral envelopes. The invention contemplates performing such lysis within the chamber optionally followed by isolation and/or manipulation of cellular contents released after lysis. Disruption can be accomplished by any number of means including chemical, enzymatic, or osmotic lysis.

In other embodiments, the agent being harvested and/or manipulated is a naturally occurring or non-naturally occurring polymer. A polymer as used herein is a compound comprised of monomers linked together by linkages. An monomer as used herein is the smallest building block that can be linked directly or indirectly to other building blocks (or monomers) to form the particular polymer. At a minimum, the polymer contains at least two linked monomers. The particular type of monomer will depend upon the type of polymer being analyzed. The polymer may be a nucleic acid, a protein, a peptide, a carbohydrate, an oligo- or polysaccharide, a lipid, etc. The polymer may be branched or unbranched. In some embodiments, the polymer is unbranched as is the case with naturally occurring nucleic acids such as genomic DNA.

In some embodiments, the polymer is capable of being bound to or by sequence- or structure-specific probes. Where the polymer and the probes are both nucleic acids and the binding is sequence specific, the probes are hybridized to the nucleic acid polymer. The probes may bind to the polymer at a sequence or structure that is unique to that polymer or to a region of that and other polymers. Polymers may also be labeled with non-sequence specific probes or labels including intercalators or non-specific dyes.

In some instances the polymers may be manipulated without prior isolation and/or purification, while in other instances the polymers may be manipulated following isolation and/or purification.

In some embodiments, the method can be used to harvest and/or manipulate a plurality of identical polymers in a sample or a plurality of different polymers in a sample.

In some important embodiments, the agents are naturally occurring or non-naturally occurring nucleic acids. Non-naturally occurring nucleic acids include but are not limited to bacterial artificial chromosomes (BACs) and yeast artificial chromosomes (YACs). The term "nucleic acid" refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). "Nucleic acid" and "nucleic acid molecule" are used interchangeably and refer to oligoribonucleotides as well as oligodeoxyribonucleotides. The terms shall also include polynucleosides (i.e., a polynucleotide minus a phosphate) and any other organic base containing nucleic acid. The organic bases include adenine, uracil, guanine, thymine, cytosine and inosine.

In important embodiments, the nucleic acid is DNA or RNA. DNA includes genomic DNA (such as nuclear DNA and mitochondrial DNA), as well as in some instances complementary DNA (cDNA). RNA includes messenger RNA (mRNA), ribosomal RNA (rRNA), microRNA (miRNA), and the like. Harvest and isolation of nucleic acids are routinely performed in the art and suitable methods can be found in standard molecular biology textbooks. (See, for example, Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981)).

Preferably, prior amplification of nucleic acids using techniques such as polymerase chain reaction (PCR) are not necessary. Accordingly, the polymer may be a non in vitro amplified nucleic acid. As used herein, a "non in vitro amplified nucleic acid" refers to a nucleic acid that has not been amplified in vitro using techniques such as polymerase chain reaction or recombinant DNA methods prior to manipulation, detection and/or analysis by the methods contemplated by the invention. A non in vitro amplified nucleic acid may however be a nucleic acid that is amplified in vivo (in the biological sample from which it was harvested) as a natural consequence of the development of the cells in vivo. This means that the non in vitro nucleic acid may be one which is amplified in vivo as part of for example locus amplification, which is commonly observed in some cell types as a result of mutation or cancer development.

As used herein, "linked" or "linkage" means two entities bound to one another by any physicochemical means. Any linkage known to those of ordinary skill in the art, covalent or non-covalent, is embraced. Natural linkages are those ordinarily found in nature connecting for example naturally occurring entities. Natural linkages include, for instance, amide, ester and thioester linkages. Nucleic acid targets or probes of the invention may comprise synthetic or modified linkages.

Nucleic acids commonly have a phosphodiester backbone because this backbone is most common in vivo. However, they are not so limited. Backbone modifications are known in the art. One of ordinary skill in the art is capable of preparing such nucleic acids without undue experimentation. The probes, if nucleic acid in nature, can also have backbone modifications such as those described herein.

Thus the nucleic acids may be heterogeneous in backbone composition thereby containing any possible combination of nucleic acid units linked together such as peptide nucleic acids (which have amino acid linkages with nucleic acid bases, and which are discussed in greater detail herein). In some embodiments, the nucleic acids are homogeneous in backbone composition.

The nucleic acids may be double-stranded, although in some embodiments the nucleic acid targets are denatured and presented in a single-stranded form. This can be accomplished by modulating the environment of a double-stranded nucleic acid including singly or in combination increasing temperature, decreasing salt concentration, and the like. Methods of denaturing nucleic acids are known in the art.

The methods of the invention in part may be used to analyze agents using probes that recognize and specifically bind to an agent. Binding of a probe to an agent may indicate the presence and location of a target site in the target agent, or it may simply indicate the presence of the agent, depending on user requirements. As used herein, a target agent that is bound by a probe is "labeled" with the probe and/or its detectable label.

As used herein, a probe is a molecule or compound that binds preferentially to the agent of interest (i.e., it has a greater affinity for the agent of interest than for other compounds). Its affinity for the agent of interest may be at least 2-fold, at least 5-fold, at least 10-fold, or more than its affinity for another compound. Probes with the greatest differential affinity are preferred in most embodiments.

The probes can be of any nature including but not limited to nucleic acid (e.g., aptamers), peptide, carbohydrate, lipid, and the like. A nucleic acid based probe such as an oligonucleotide can be used to recognize and bind DNA or RNA. The nucleic acid based probe can be DNA, RNA, LNA or PNA, although it is not so limited. It can also be a combination of one or more of these elements and/or can comprise other nucleic acid mimics. With the advent of aptamer technology, it is possible to use nucleic acid based probes in order to recognize and bind a variety of non-nucleic acid agents, including peptides and carbohydrates, in a structurally specific manner. Other probes for nucleic acid agents include but are not limited to sequence-specific major and minor groove binders and intercalators, nucleic acid binding peptides or proteins, etc.

As used herein a "peptide" is a polymer of amino acids connected preferably but not solely with peptide bonds. The probe may be an antibody or an antigen-binding antibody fragment. Antibodies include IgG, IgA, IgM, IgE, IgD as well as antibody variants such as single chain antibodies. Antigen-binding antibody fragments include but are not limited to Fab, $F(ab)_2$, and Fv fragments.

The methods provided herein involve the use of probes that bind to the target polymer in a sequence-specific manner. "Sequence-specific" when used in the context of a nucleic acid means that the probe recognizes a particular linear (or in some instances quasi-linear) arrangement of nucleotides or derivatives thereof. In some embodiments, the probes are "polymer-specific" meaning that they bind specifically to a particular polymer, possibly by virtue of a particular sequence or structure unique to that polymer. The degree of specificity with which the probes bind to target agents will depend on the conditions in which the binding (or hybridization) occurs. For example, salt concentration and temperature can be modulated in order to vary the range of sequences recognized by the nucleic acid probes. Generally speaking the more stringent the conditions, the more specific the binding and the less likely will be the occurrence of non-specific binding events. Those of ordinary skill in the art will be able to determine optimum conditions for a desired specificity.

In some instances, nucleic acid probes will form at least a Watson-Crick bond with a target nucleic acid. In other instances, the nucleic acid probe can form a Hoogsteen bond with the target nucleic acid, thereby forming a triplex. A nucleic acid probe that binds by Hoogsteen binding enters the major groove of a nucleic acid polymer and hybridizes with the bases located there. Examples of these latter probes include molecules that recognize and bind to the minor and major grooves of nucleic acids (e.g., some forms of antibiotics). In some embodiments, the nucleic acid probes can form both Watson-Crick and Hoogsteen bonds with the nucleic acid polymer. BisPNA probes, for instance, are capable of both Watson-Crick and Hoogsteen binding to a nucleic acid.

The length of probe can also determine the specificity of binding. The energetic cost of a single mismatch between the probe and the nucleic acid polymer is relatively higher for shorter sequences than for longer ones. Therefore, hybridization of smaller nucleic acid probes is more specific than is hybridization of longer nucleic acid probes because the longer probes can embrace mismatches and still continue to bind to the polymer depending on the conditions. One potential limitation to the use of shorter probes however is their inherently lower stability at a given temperature and salt concentration. In order to avoid this latter limitation, bisPNA probes can be used to bind shorter sequences with sufficient hybrid stability. Longer probes are desirable when unique gene-specific sequences are being detected.

Notwithstanding these provisos, the nucleic acid probes of the invention can be any length ranging from at least 4 nucleotides to in excess of 1000 nucleotides. The length of the probe can be any length of nucleotides between and including the ranges listed herein, as if each and every length was explicitly recited herein. Thus, the length may be at least 5 nucleotides, at least 10 nucleotides, at least 15 nucleotides, at least 20 nucleotides, or at least 25 nucleotides, or more, in length. The length may range from at least 4, at least 5, at least 6, at least 7, at least 8, at least 9, at least 10, at least 12, at least 15, at least 20, at least 25, at least 50, at least 75, at least 100, at least 150, at least 200, at least 250, at least 500, or more nucleotides (including every integer therebetween as if explicitly recited herein). In preferred embodiments, the probes are 5-100 nucleotides in length, more preferably between 5-25 nucleotides in length, and even more preferably 5-12 nucleotides in length.

The probes are preferably single-stranded, but they are not so limited. For example, when the probe is a bisPNA it can adopt a secondary structure with the nucleic acid polymer resulting in a triple helix conformation, with one region of the bisPNA clamp forming Hoogsteen bonds with the backbone of the polymer and another region of the bisPNA clamp forming Watson-Crick bonds with the nucleotide bases of the polymer.

In some embodiments, the probes may be molecular beacons. When not bound to their targets, the molecular beacon probes form a hairpin structure and do not emit fluorescence since one end of the molecular beacon is a quencher molecule. However, when bound to their targets, the fluorescent and quenching ends of the probe are sufficiently separated so that the fluorescent end can now emit.

In some embodiments, the probe is a nucleic acid that is a peptide nucleic acid (PNA), a bisPNA clamp, a pseudocomplementary PNA, a locked nucleic acid (LNA), DNA, RNA, or co-nucleic acids of the above such as DNA-LNA co-nucleic acids. siRNA or miRNA or RNAi molecules can be similarly used.

In some embodiments, the probe is a peptide nucleic acid (PNA), a bisPNA clamp, a locked nucleic acid (LNA), a ssPNA, a pseudocomplementary PNA (pcPNA), a two-armed PNA (as described in co-pending U.S. patent application having Ser. No. 10/421,644 and publication number US 2003-0215864 A1 and published Nov. 20, 2003, and PCT application having serial number PCT/US03/12480 and publication number WO 03/091455 A1 and published Nov. 6, 2003, filed on Apr. 23, 2003), or co-polymers thereof (e.g., a DNA-LNA co-polymer).

PNAs are DNA analogs having their phosphate backbone replaced with 2-aminoethyl glycine residues linked to nucleotide bases through glycine amino nitrogen and methylenecarbonyl linkers. PNAs can bind to both DNA and RNA targets by Watson-Crick base pairing, and in so doing form stronger hybrids than would be possible with DNA or RNA based probes. BisPNA includes two strands connected with a flexible linker. One strand is designed to hybridize with DNA by a classic Watson-Crick pairing, and the second is designed to hybridize with a Hoogsteen pairing. Pseudocomplementary PNA (pcPNA) (Izvolsky, K. I. et al., *Biochemistry* 10908-10913 (2000)) involves two single stranded PNAs added to dsDNA. Locked nucleic acid (LNA) molecules form hybrids with DNA, which are at least as stable as PNA/DNA hybrids (Braasch, D. A. et al., *Chem & Biol.* 8(1):1-7(2001)).

As stated herein, the agent may be labeled. As an example, if the agent is a nucleic acid, it may be labeled through the use of sequence-specific probes that bind to the polymer in a sequence-specific manner. The sequence-specific probes are labeled with a detectable label (e.g., a fluorophore or a radioisotope). The nucleic acid however can also be synthesized in a manner that incorporates detectable labels such as fluorophores directly into the growing nucleic acid. Nucleic acids can be synthesized de novo (e.g., using automated nucleic acid synthesizers) using fluorescently labeled nucleotides. Such nucleotides are commercially available from suppliers such as Amersham Biosciences, Invitrogen, and New England Nuclear/Perkin Elmer.

Alternatively, nucleic acids may be synthesized or modified post synthesis to include active amino or thiol groups. (Proudnikov and Mirabekov, Nucleic Acid Research, 24:4535-4532, 1996.) An extensive description of modification procedures that can be performed on a nucleic acid polymer can be found in Hermanson, G. T., Bioconjugate Techniques, Academic Press, Inc., San Diego, 1996, which is incorporated by reference herein. There are several known methods of direct chemical labeling of DNA (Hermanson, 1996; Roget et al., 1989; Proudnikov and Mirabekov, 1996). One of the methods is based on the introduction of aldehyde groups by partial depurination of DNA. Fluorescent labels with an attached hydrazine group are efficiently coupled with the aldehyde groups and the hydrazine bonds are stabilized by reduction with sodium labeling efficiencies around 60%. The reaction of cytosine with bisulfite in the presence of an excess of an amine fluorophore leads to transamination at the N4 position (Hermanson, 1996). Reaction conditions such as pH, amine fluorophore concentration, incubation time, and temperature affect the yield of products formed.

Probes are generally labeled with a detectable label. A detectable label is a moiety, the presence of which can be ascertained directly or indirectly. Generally, detection of the label involves the creation of a detectable signal such as for example an emission of energy. The label may be of a chemical, peptide or nucleic acid nature although it is not so limited.

The nature of the label used will depend on a variety of factors, including the nature of the analysis being conducted, the type of energy source and detector used, and the type of polymer and probe. The label should be sterically and chemically compatible with the entities to which it is bound.

The label can be detected directly for example by its ability to emit and/or absorb electromagnetic radiation of a particular wavelength. A label can be detected indirectly for example by its ability to bind, recruit and, in some cases, cleave another moiety which itself may emit or absorb light of a particular wavelength (e.g., an epitope tag such as the FLAG epitope, an enzyme tag such as horseradish peroxidase, etc.). Generally the detectable label can be selected from the group consisting of directly detectable labels such as a fluorescent molecule (e.g., fluorescein, rhodamine, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), 5-(2'-aminoethyl) aminonaphthalene-1-sulfonic acid (EDANS), 4-acetamido-4'-isothiocyanatostilbene-2,2'disulfonic acid, acridine, acridine isothiocyanate, r-amino-N-(3-vinylsulfonyl)phenylnaphthalimide-3,5, disulfonate (Lucifer Yellow VS), N-(4-anilino-1-naphthyl)maleitnide, anthranilamide, Brilliant Yellow, coumarin, 7-amino-4-methylcoumarin, 7-amino-4-trifluoromethylcouluarin (Coumarin 151), cyanosine, 4',6-diaminidino-2-phenylindole (DAPI), 5',5"-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stibene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6-dichlorotriazin-2-yl) aminofluorescein (DTAF), QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron® Brilliant Red 3B-A), lissamine rhodamine B sulfonyl chloride, rhodamine B, rhodamine 123, rhodamine X, sulforhodamine B, sulforhodamine 101, sulfonyl chloride derivative of sulforhodamine 101, tetramethyl rhodamine, riboflavin, rosolic acid, and terbium chelate derivatives), a chemiluminescent molecule, a bioluminescent molecule, a chromogenic molecule, a radioisotope (e.g., $P^{32}$ or $H^3$, $^{14}C$, $^{125}I$ and $^{131}I$), an electron spin resonance molecule (such as for example nitroxyl radicals), an optical or electron density molecule, an electrical charge transducing or transferring molecule, an electromagnetic molecule such as a magnetic or paramagnetic bead or particle, a semiconductor nanocrystal or nanoparticle (such as quantum dots described for example in U.S. Pat. No. 6,207,392 and commercially available from Quantum Dot Corporation and Evident Technologies), a colloidal metal, a colloid gold nanocrystal, a nuclear magnetic resonance molecule, and the like.

The detectable label can also be selected from the group consisting of indirectly detectable labels such as an enzyme (e.g., alkaline phosphatase, horseradish peroxidase, β-galactosidase, glucoamylase, lysozyme, luciferases such as firefly luciferase and bacterial luciferase (U.S. Pat. No. 4,737,456); saccharide oxidases such as glucose oxidase, galactose oxidase, and glucose-6-phosphate dehydrogenase; heterocyclic oxidases such as uricase and xanthine oxidase coupled to an enzyme that uses hydrogen peroxide to oxidize a dye precursor such as HRP, lactoperoxidase, or microperoxidase), an enzyme substrate, an affinity molecule, a ligand, a receptor, a biotin molecule, an avidin molecule, a streptavidin molecule, an antigen (e.g., epitope tags such as the FLAG or HA epitope), a hapten (e.g., biotin, pyridoxal, digoxigenin fluorescein and dinitrophenol), an antibody, an antibody fragment, a microbead, and the like. Antibody fragments include Fab, $F(ab)_2$, Fd and antibody fragments which include a CDR3 region.

In some embodiments, the detectable label is a member of a FRET fluorophore pair. FRET fluorophore pairs are two fluorophores that are capable of undergoing FRET to produce or eliminate a detectable signal when positioned in proximity to one another. Examples of donors include Alexa 488, Alexa 546, BODIPY 493, Oyster 556, Fluor (FAM), Cy3 and TMR (Tamra). Examples of acceptors include Cy5, Alexa 594, Alexa 647 and Oyster 656. Cy5 can work as a donor with Cy3, TMR or Alexa 546, as an example. FRET should be possible with any fluorophore pair having fluorescence maxima spaced at 50-100 nm from each other.

The polymer may be labeled in a non-sequence-specific manner. For example, if the polymer is a nucleic acid such as DNA, then its backbone may be stained with a backbone label. Examples of backbone stains that label nucleic acids in a sequence non-specific manner include intercalating dyes (or intercalators) such as phenanthridines and acridines (e.g., ethidium bromide, propidium iodide, hexidium iodide, dihydroethidium, ethidium homodimer-1 and -2, ethidium monoazide, and ACMA); minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Invitrogen.

Still other examples of nucleic acid stains include the following dyes from Invitrogen: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the invention. The advantages and objects of the invention are not necessarily encompassed by each embodiment of the invention.

The present invention is further illustrated by the following Examples, which in no way should be construed as further limiting.

EXAMPLES

Example 1

Chamber Construction

One chamber embodiment includes a circular substrate that has an exposed surface area of about 95 mm2, and a flow region volume of 140 mL. The chamber is configured generally as shown in FIGS. 1a and 1b, except that the chamber includes only two side ports, positioned on opposed sides of the flow region. The chamber operates during a separation mode with a flow rate of about 0.63 mL/min through the central port, toughly 0.05 mL/min passes through the substrate while the remaining flow (0.58 mL/min) is diverted through the side ports. This configuration has been found to effectively hold 15 kilobase to 5 Megabase DNA on or about the substrate, under these operating conditions.

Example 2

Operating Protocol for DNA Isolation and Digestion in a Chamber, as Shown in FIG. 6, Using the Chamber of Example 1

1. Injection of cells. A sample of *E. coli* cells is introduced directly into the chamber in a press down mode, as shown in 6a. The chamber waste ports are open while the side ports are closed. The solvent can pass through the substrate while the *E. coli* cells are retained inside the chamber substantially uniformly distributed on the substrate. The chamber is maintained at the appropriate temperature for lysis. Flow through the central port is 0.1 mL/min and the temperature of the flow region is maintained at 37° C.

2. Washing. The buffer of the sample can be exchanged with lysis buffer, in a separation mode, by introducing lysis buffer containing detergents such as laurylsarcosine and Triton. The buffer is injected through the central port. The excess liquid is removed through the waste ports and the side ports in a separation mode. An appropriate ratio of the waste and side port flow rates is maintained that allows the cells to be held at the substrate inside the chamber without disturbing their distribution. Flow through the central port is 0.63 mL/min, flow through the side ports is 0.58 mL/min, flow through the substrate is 0.05 mL/min, and the temperature is maintained at 37° C.

Figure 6A:
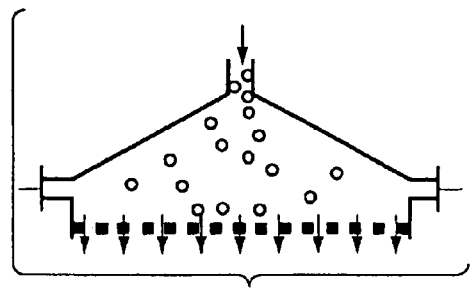
FIGS. 6a-6h show, schematically, various stages of an operating protocol for DNA isolation and digestion in a chamber.
Figure 6E:
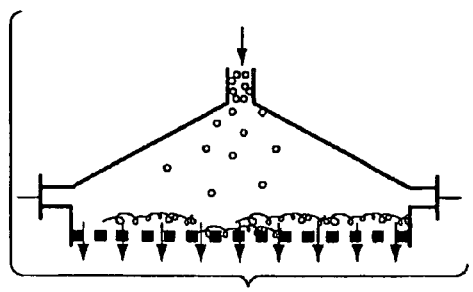
Figure 6B:
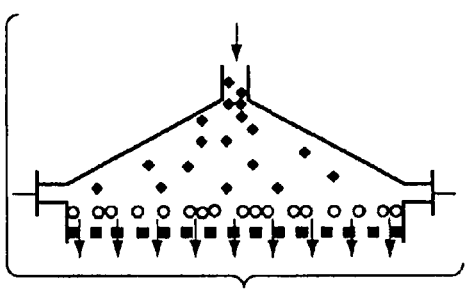

3. Injection of lytic enzymes. Lysis buffer containing lysozyme is introduced through the central port, in a press down mode, as shown in FIG. 6b. The excess liquid passes through the substrate and is removed through the waste ports. The side ports remain closed. The *E. coli* cells remain immobilized on the substrate. The enzymes accumulate at the substrate with a concentration gradient extending within tens of microns into the flow region from the substrate. Flow through the central port is 0.05 mL/min and the temperature is maintained at 37° C.

Figure 6F:
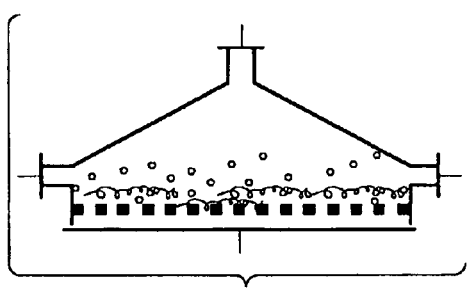
Figure 6C:
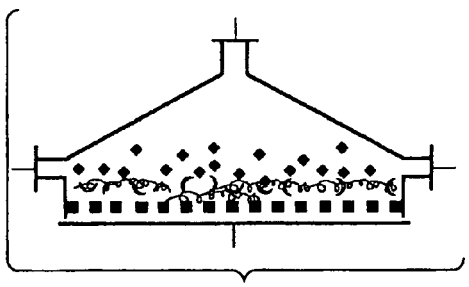

4. Lysis. Lysis is allowed to proceed in a substantially quiescent chamber, in a reaction mode, as shown in FIG. 6c. The result is the release of genomic DNA and waste materials (e.g., cellular debris). The temperature is maintained at 37° C.

5. Injection of Proteinase k. Buffer containing proteinase K is introduced through the central port, in a press down mode, as shown in FIG. 6b. The excess liquid passes through the substrate and is removed through the waste ports. The side ports remain closed. The *E. coli* cells remain immobilized on the substrate. The enzymes accumulate at the substrate with a concentration gradient extending within tens of microns into the flow region from the substrate. Flow through the central port is 0.05 mL/min and the temperature is maintained at 37° C.

6. Proeteinase k Digestion. Proeteinase k digestion is allowed to proceed in a substantially quiescent chamber, in a reaction mode, as shown in FIG. 6c. The temperature is maintained at 55° C.

Figure 6G:
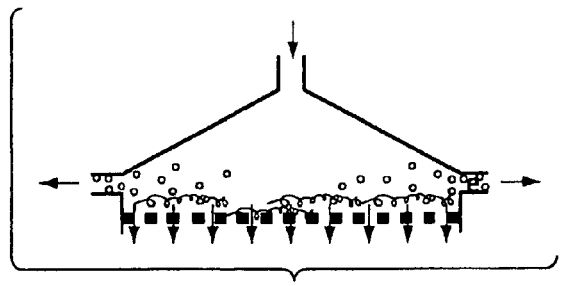
Figure 6D:
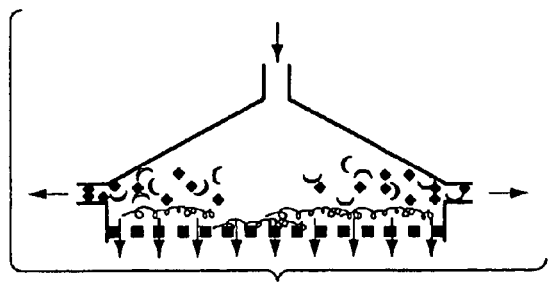

7. Washing. Buffer is introduced through the central port to remove unwanted materials from the flow region in a separation mode, as shown in FIG. 6d. Again, the excess liquid carrying the waste is removed through the waste ports and the side ports maintaining an appropriate ratio of the two flows. The Megabase genomic DNA, which is larger than the threshold size of the substrate, is held by the flow through the substrate. Several buffers can be used consecutively in this step to achieve the desired purification level. The last buffer introduced is the buffer required for restriction enzyme digestion. The flow rate through the central port is 0.63 mL/min, the flow rate though the side ports is 0.58 mL/min, and the flow through the substrate is 0.05 mL/min. The temperature is maintained at 37° C.

8. Introduction of restriction enzyme. Restriction enzyme is introduced the chamber through the central port in a press down mode, as shown in FIG. 6e. The flow rate through the central port is 0.05 mL/min and the flow through the substrate is 0.05 mL/min. The temperature is maintained at 37° C.

7. Restriction. Digestion is allowed to proceed in an enclosed system, in a reaction mode, as shown in FIG. 6f. The result is digestion of genomic DNA into smaller fragments. There is no flow through the chamber and the temperature is maintained at an appropriate temperature for the chosen restriction enzyme.

8. Washing. Buffer is introduced through the central port to remove the restriction enzyme and exchange the restriction enzyme buffer with elution buffer, in a separation mode, as shown in FIG. 6g. Several buffers can be used consecutively in this step to achieve the desired purification level. The last buffer introduced is the buffer for elution. The flow rate through the central port is 0.63 mL/min, the flow rate though the side ports is 0.58 mL/min, and the flow through the substrate is 0.05 mL/min. The temperature is maintained at 37° C.

Figure 6H:
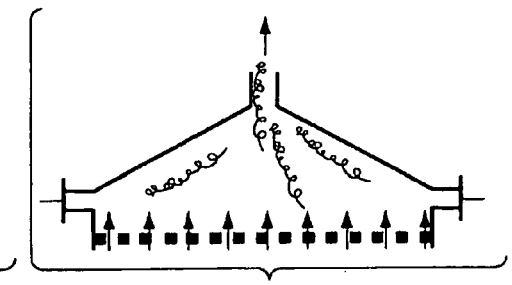
Figure 8:
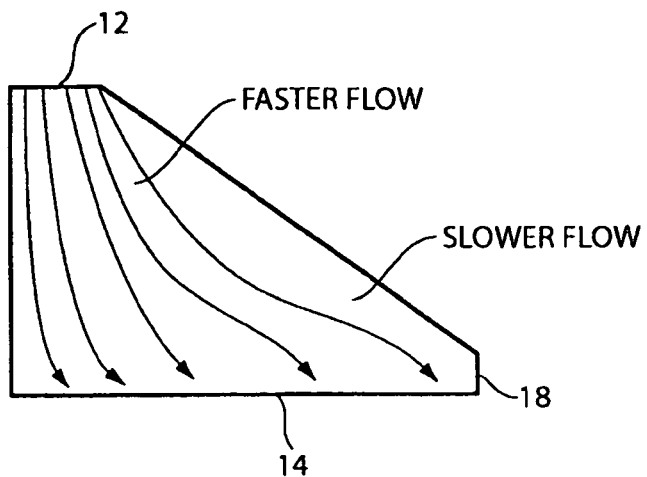
FIGS. 8-12 show visual representations of modeling results discussed with respect to Example 7.

9. Elution. Buffer is added to the chamber through one of the side ports and genomic DNA is eluted from the chamber through the central port, in an elution mode, as shown in FIG. 6h. The side ports remain closed. The elution flow rate is 0.1 mL/min. The temperature is room temperature.

10. The reaction chamber is now ready to isolate DNA from another sample.

Example 3

Results from Using an Operating Protocol Like that Described in Example 2

FIG. 7 shows representations of genomic DNA from *Bacillus* spores and *E. coli* cells isolated and digested in the reaction chamber following a protocol similar to the example protocol described above with respect to Example 2, and illustrates pulsed field gel of elution fractions from the reaction chamber. Lane 1 shows lambda ladder used as a size marker, lane 2-4 show the first three elution fractions. Slide A shows DNA fragments from decoated *Bacillus* spores that were introduced into the reaction chamber and DNA was isolated, purified, digested with NotI and eluted by reverse flow elution through the central port. All expected fragments are present. Slide B shows DNA fragments from *E. coli* cells which were introduced into the reaction chamber and subjected to spore decoating, lysis, purification, and NotI digestion. Genomic DNA was recovered by reverse flow elution through the central port. All expected fragments are present. Slide C shows DNA fragments from a mixture of *Bacillus* spores and *E. coli* cells that were introduced into the chamber and subjected to spore decoating, lysis, DNA purification and NotI digestion. Digested genomic DNA from both organisms was recovered by reverse flow elution through the central port. The digestion pattern is clearly a sum of *Bacillus* and *E. coli* fragments.

Example 4

Operating Protocol for Circular Plasmid/BAC Isolation and Purification in a Chamber, Using the Chamber of Example 1

Injection of cells. A sample of *E. coli* cells is introduced into the chamber in a press down mode. The chamber waste ports are open while the side ports are closed. The solvent can pass through the substrate while the *E. coli* cells are retained inside the chamber uniformly distributed on the substrate. The chamber is maintained at the appropriate temperature for lysis.

Washing. The buffer of the sample can be exchanged with lysis buffer by introducing lysis buffer containing detergents such as laurylsarcosine and Triton. The buffer is introduced through the central port. The excess liquid is removed through the waste ports and the side ports. An appropriate ratio of the waste and side port flow rates is maintained in a separation mode to allow the cells to be held at the substrate inside the chamber without disturbing their distribution.

Injection of lytic enzymes. Lysis buffer containing lysozyme is introduced through the central port, in a press down mode. The excess liquid passes through the substrate and is removed through the waste ports. The side ports remain closed. The *E. coli* cells remain immobilized on the substrate. The enzymes accumulate at the substrate with a concentration gradient extending within tens of microns into the flow region from the substrate. Flow through the central port is 0.05 mL/min and the temperature is maintained at 37° C.

Lysis. Lysis is allowed to proceed in a substantially quiescent chamber, in a reaction mode. The result is the release of genomic DNA and waste materials (e.g., cellular debris). The temperature is maintained at 37° C.

Injection of Proteinase k. Buffer containing proteinase K is introduced through the central port, in a press down mode. The excess liquid passes through the substrate and is removed through the waste ports. The side ports remain closed. The *E. coli* cells remain immobilized on the substrate. The enzymes accumulate at the substrate with a concentration gradient extending within tens of microns into the flow region from the substrate. Flow through the central port is 0.05 mL/min and the temperature is maintained at 37° C.

Proeteinase k Digestion. Proeteinase k digestion is allowed to proceed in a substantially quiescent chamber, in a reaction mode. The temperature is maintained at 55° C.

Washing. Buffer is introduced through the central port to remove all unwanted materials in a separation mode. The excess liquid carrying the waste is removed through the waste ports and the side ports maintaining an appropriate ratio of the two flows. The DNA is held by the substrate. Several buffers can be used consecutively in this step to achieve the desired purification level. The last buffer introduced is the buffer required for exonuclease digestion.

Injection of restriction enzyme and exonuclease. A DNA exonuclease and a DNA endonuclease are introduced into the chamber in a press down mode. The endonuclease is selected such that it will have recognition site(s) only on the genomic DNA.

Digestion of genomic DNA. Digestion is allowed to proceed in a substantially quiescent system in a reaction mode. At the end of this step, the temperature of the chamber is raised for the appropriate time to inactivate the exconuclease.

Washing. Buffer is introduced through the central port to remove all unwanted materials in a separation mode. Again, the excess liquid carrying the waste is removed through the waste ports and the side ports maintaining an appropriate ratio of the two flows. To keep the plasmid/BAC DNA inside the chamber. Several buffers can be used consecutively in this step to achieve the desired purification level. The last buffer introduced is the buffer required for elution.

Elution. Plasmid/BAC DNA is eluted from the chamber.

Example 5

Operating Protocol for DNA Tagging in a Chamber Like that of Example 1

Injection of DNA. A sample of DNA is introduced directly into the chamber in a press down mode. The chamber waste ports are open while the side ports are closed. The solvent can pass through the substrate while the DNA molecules are retained inside the chamber uniformly distributed on the substrate.

Washing. The buffer of the sample can be exchanged with tagging buffer in a separation mode. The buffer is introduced through the central port. The excess liquid is removed through the waste ports and the side ports. An appropriate ratio of the waste and side port flow rates is maintained that allows the DNA to be held at the substrate inside the chamber without disturbing its distribution.

Injection of tags. Sequence specific DNA tags (e.g. fluorescently labeled bis-PNA or fluorescently modified restriction enzymes) are introduced through the central port in a press down mode. The excess liquid passes through the substrate and is removed through the waste ports. The side ports remain closed. The DNA molecules remain immobilized on the substrate.

Tagging. Tagging is allowed to proceed in a substantially quiescent system, in a reaction mode. Alternatively, tagging may be performed using slow injection flow through the central port and the waste ports only. The chamber temperature is maintained at the appropriate value for the tagging reaction.

Washing. Buffer is introduced through the central port to remove excess free tags in a separation mode. Again, the excess liquid carrying the waste is removed through the waste ports and the side ports maintaining an appropriate ratio of the two flows. Several buffers can be used consecutively in this step to achieve the desired purification level. In the case of bis-PNA tagging the buffer may contain high salt concentration to assist the removal of non-specifically bound tags. In the case of restriction enzyme tags the tagging buffer can be used in this step.

Removal of non-specifically bound tags. The removal of non-specifically bound tags can be carried out in a reaction mode in a substantially quiescent system. The chamber temperature is maintained at the appropriate value which will allow fast disassociation of non-specifically bound tags.

Washing. Buffer is introduced through the central port in a separation mode to remove any residual excess free tags and to introduce the desired elution buffer in an elution mode.

Elution. Tagged DNA eluted from the chamber.

Example 6

Modeling of Flow in a Chamber

Models and simulations were used to optimize the design and function of an embodiment of the chamber. The models focused on flow fields for manipulating genomic sized DNA with minimal or no shear degradation. Microbes and free flowing DNA were modeled as rigid particles whereas semi-dilute DNA solution immobilized on the substrate was modeled according to the reptation model of Doi and Edwards. The nomenclature used in reporting the modeling results of Example 7 is shown below in Table 1.

TABLE 1

| Nomenclature | |
| --- | --- |
| Vz | Axial downward direction velocity (m/s) |
| z | Distance perpendicular from the substrate in um (axial direction) |
| Q | Flow rate (mL/min) |
| Vr | Radial direction velocity (m/s) |
| r | Radial distance from the central axis of the chamber (m) |
| rho | Particle density (g/cm3) |
| z90 | Axial distance from the substrate that includes 90% of reactants |

Figure 9:
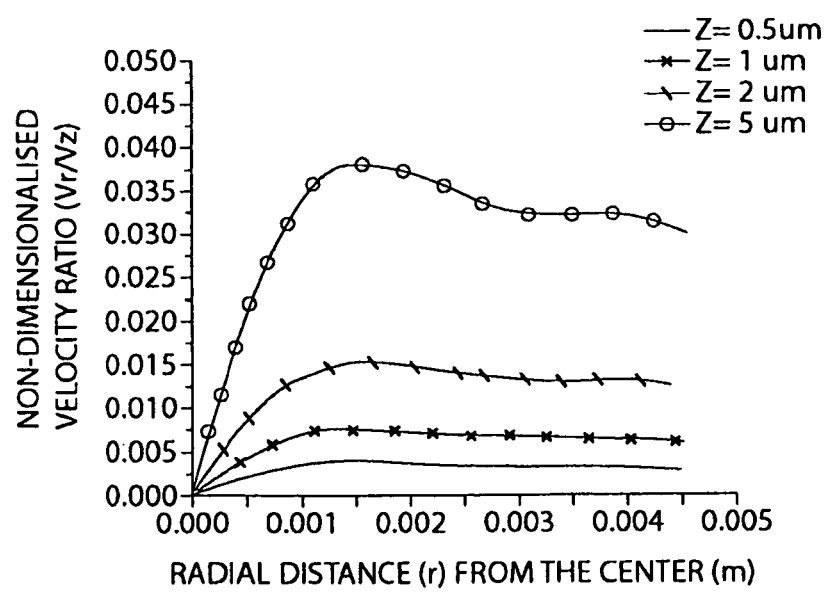
Figure 10:
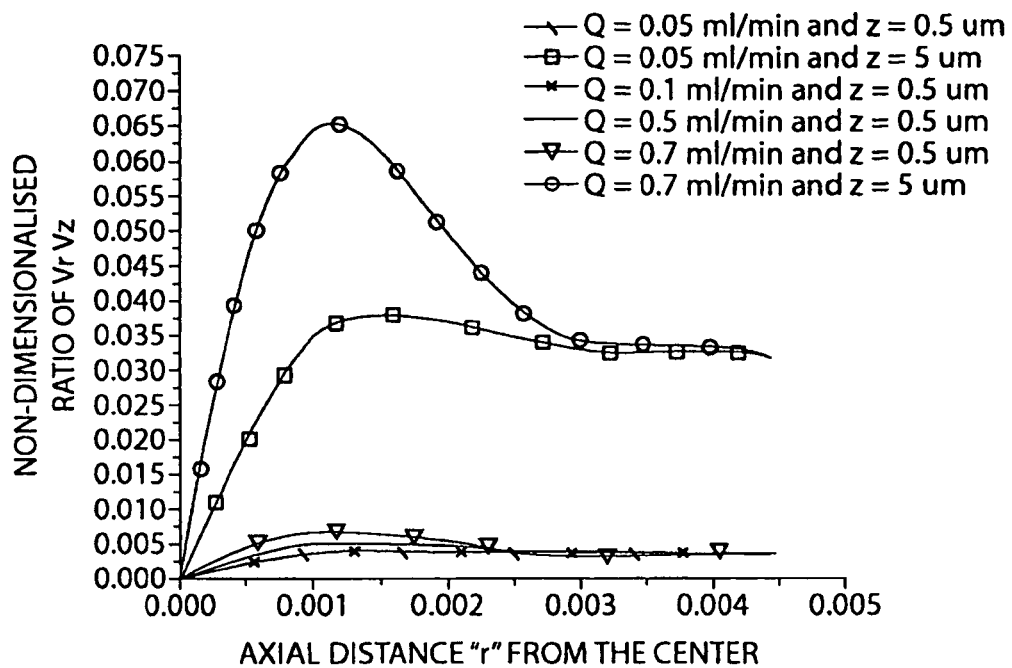

FIG. 7 shows a simulation of injection flow in the chamber. This particular geometry that is illustrated was optimized for injection flow rates ≤0.7 mL/min. Bending of the flow stream lines, as shown, is attributed to a change from a parabolic velocity profile in the diffuser section to a more uniform velocity profile at the substrate surface. This bending can disturb reactants that are distributed on or about the substrate surface. To prevent this disturbance, the ratio of the radial (r) velocity component to the normal (z) velocity component may be minimized so that the fluidic drag force in the downward (z) direction is larger as compared to the drag force in the radial direction. FIGS. 9 and 10 show that this criterion is met in the chamber for a range of flow rates through the central port that are typically used. Meeting this requirement allows reagents to be introduced through the central port sequentially without disturbing a layer of agents that are already spread about the substrate. In FIG. 9, the ratio Vr/Vz versus radial distance is shown for Q=0.05 ml/min. FIG. 10 shows the variation of Vr/Vz ratio with flow rates through the central port.

Figure 11:
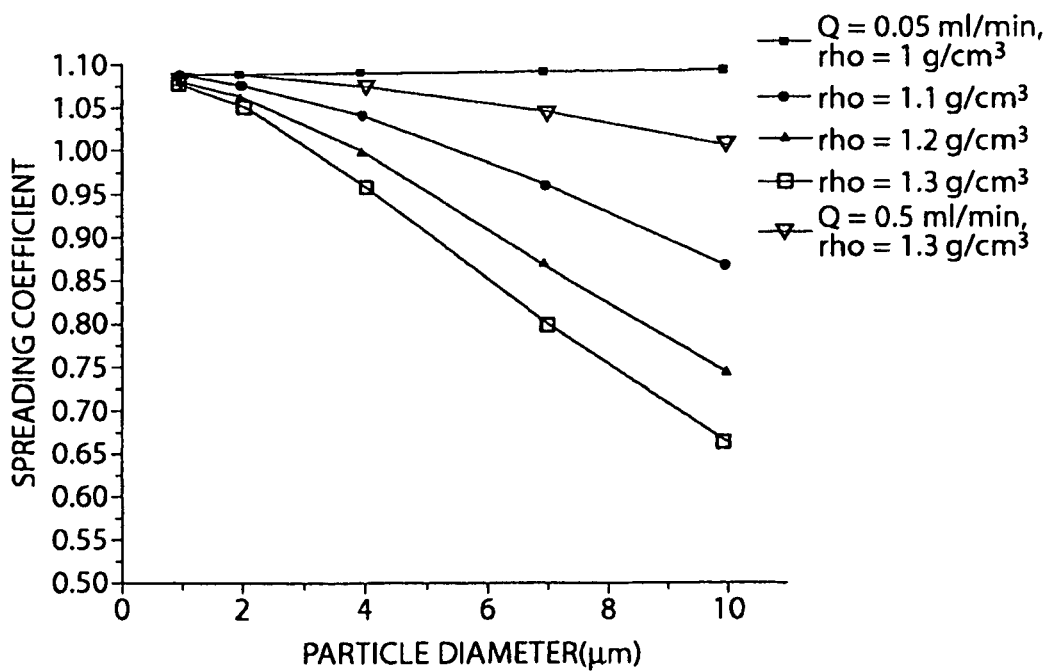

Modeling shows that there may be an upper limit on the size and density of particles that will follow the flow within the chamber to spread uniformly about the substrate in a press down mode. FIG. 11 shows the spreading of particles as a function of particle diameter, particle density (rho) and flow rate (Q) through the central port. The modeling calculations are based on the assumption that the particles are in the dilute regime i.e. the inter-particle distance is larger than particle radius, such that particle-particle interactions may be neglected.

Figure 12:
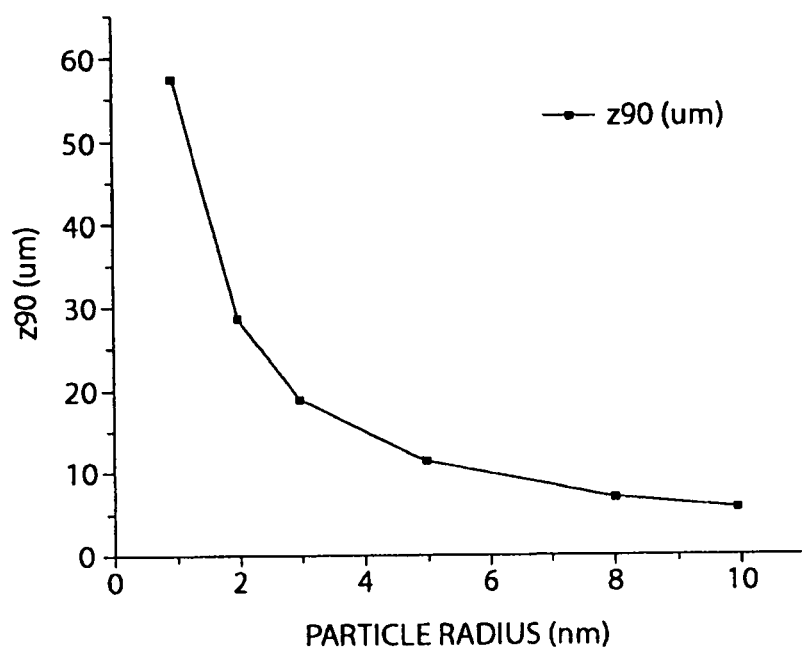

Modeling confirmed that downward flow fields exert a downward force on particles in the chamber, which can be used to hold agents on or about the substrate, even against the upward diffusion of agents, which may also be occurring within the chamber. FIG. 11 shows the variation of spreading coefficient versus particle diameter. Spreading coefficient was estimated by releasing a particle at r=0.9 mm at the central port and tracking the final radial distance of that particle on the substrate. a measure of the confinement region of reagents about the substrate. FIG. 11 illustrates the axial distance 'z' from the substrate below which 90% of the reagents are confined. The model assumes no passage of reagents through the substrate. FIG. 12 shows that the chamber may be used to create a micro-reaction zone within the chamber (FIG. 12 is representative for Q=0.05 mL/min. This micro-reaction zone may be used to enhance reaction rates.

Example 7

Operating Times for an Operating Protocol that Involves Isolation of Bacterial Genomic DNA Table 2 shows times associated with isolation of bacterial genomic DNA performed in a chamber, like that described herein with respect to Example 1, and compares processing times for portions of the operating protocol with a conventional test tube protocol.

TABLE 2

| Test tube protocol | Time | Operating Protocol for Chamber | Time |
|---|---|---|---|
| Pellet 1x108 cells | 10 minutes | Inject 1x108 cells in a press down mode | 5 minutes |
| Wash cells and pellet again | 20 minutes | Wash cells in a separation mode | 0 minutes |
| Resuspend in lysozyme containing buffer and incubate | 4-16 hours | Introduce lysozyme in a press down mode and incubate | 25 minutes |
| Add proteinase K and buffer and incubate | 6-48 hours | Intorduce proteinase K in a press down mode and incubate | 26 minutes |
| Dialyse | 20-48 hours | Wash in a separation mode | 25 minutes |
| Add restriction enzyme and incubate | 4-16 hour | Introduce restriction enzyme in a press down mode and incubate | 26 minutes |
| Dialyse | 16 hours | wash in a separation mode | 18 minutes |
| Total Time | >50 hours | Total Time | 2 hours, 5 minutes |

Example 8

Operating Times for an Operating Protocol that Involves Tagging of DNA with Bis-PNA Table 3 shows times associated with the tagging of DNA with bis-PNA performed in a chamber, like that described herein with respect to Example 1, and compares processing times for portions of the operating protocol with a conventional test tube protocol.

TABLE 3

| Test tube protocol | Time | Operating Protocol for Chamber | Time |
|---|---|---|---|
| Mix DNA and bis-PNA and incubate | 1.2 hours. | Introduce DNA and bis-PNA to chamber in a press down mode and incubate | 37 minutes |
| Dialyze excess bis-PNA | 17 hours | Wash excess bis-PNA in a separation mode | 14 minutes |
| After-heating | 0.2-1 hour | After heating in chamber Wash in a separation mode | 12 minutes 27 minutes |
| Total Time | >18 hours | Total Time | 1.5 hours |

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A system for separating agents from non-agents in a chamber, the system comprising:
a chamber comprising:
a fluid introduction port;
a porous substrate positioned substantially opposite from the fluid introduction port in the chamber, the porous substrate configured to prevent the passage of agents that are larger than a threshold size of the porous substrate, the porous substrate having a first side and a second side, wherein the fluid introduction port is positioned on the first side of the porous substrate;
a plurality of ports coupled to the chamber and configured to permit fluid to exit the chamber, wherein the plurality of ports includes at least a first port, a second port, and a third port, wherein the first port and the second port are positioned on the first side of the porous substrate and the third port is positioned on the second side of the porous substrate, and wherein the first port is substantially parallel to a surface of the porous substrate;
a controller configured to control:
a first flow of fluid into the chamber from the fluid introduction port and through the porous substrate to hold agents and other constituents at the porous substrate; and
a second flow of fluid into the chamber from the fluid introduction port and through at least one of the first and second ports to allow other constituents to move away from the agents on the porous substrate.

2. The system of claim 1, wherein the controller is configured to reduce the second flow relative to the first flow to direct agents towards the porous substrate when agents are introduced to the chamber through the fluid introduction port.

3. The system of claim 1, wherein the controller is configured to increase the second flow relative to the first flow to move other constituents away from the agents on the porous substrate.

4. The system of claim 1, wherein the controller is configured to substantially stop the first and second flows through the chamber to allow reactions to occur between the agents and other constituents.

5. The system of claim 1, wherein the controller is configured to reverse the first flow to move the agents away from the porous substrate and towards the fluid introduction port.

6. The system of claim 1, wherein the agents comprise nucleic acids that have been separated from one or more cells from which the nucleic acids were originally presented.

7. The system of claim 1, wherein the other constituents are selected from the group comprising: sequence specific probes, intercalators, cellular debris, lytic enzymes, endonucleases, and exonucleases.

8. The system of claim 1, wherein the agents comprise proteins.

9. The system of claim 1, wherein the controller is configured to automatically control the first flow and the second flow according to an operating protocol.

10. The system of claim 1, wherein the chamber has a substantially truncated cone shape.

11. A system for separating agents from non-agents in a chamber, the system comprising:
a chamber comprising:
a fluid introduction port;
a porous substrate positioned substantially opposite from the fluid introduction port in the chamber, the porous substrate configured to prevent the passage of agents that are larger than a threshold size of the porous substrate, the porous substrate having a first side and a second side, wherein the fluid introduction port is positioned on the first side of the porous substrate;
a plurality of ports coupled to the chamber and configured to permit fluid to exit the chamber, wherein the plurality of ports includes at least a first port, a second port, a third port and a fourth port, wherein the first port and the second port are positioned on the first side of the porous substrate and the third port and the fourth port are positioned on the second side of the porous substrate;
a controller configured to control:
a first flow of fluid into the chamber from the fluid introduction port and through the porous substrate to hold agents and other constituents at the porous substrate; and
a second flow of fluid into the chamber from the fluid introduction port and through at least one of the first and second ports to allow other constituents to move away from the agents on the porous substrate.

12. The system of claim 11, wherein the chamber has a substantially truncated cone shape.

13. A system for separating agents from non-agents in a chamber, the system comprising:
a chamber with a substantially truncated cone shape, the chamber comprising:
a fluid introduction port;
a porous substrate positioned substantially opposite from the fluid introduction port in the chamber, the porous substrate configured to prevent the passage of agents that are larger than a threshold size of the porous substrate, the porous substrate having a first side and a second side, wherein the fluid introduction port is positioned on the first side of the porous substrate;
a plurality of ports coupled to the chamber and configured to permit fluid to exit the chamber, wherein the plurality of ports includes at least a first port, a second port and a third port, wherein the first port and the second port are positioned on the first side of the porous substrate and the third port is positioned on the second side of the porous substrate;
a controller configured to control:
a first flow of fluid into the chamber from the fluid introduction port and through the porous substrate to hold agents and other constituents at the porous substrate; and
a second flow of fluid into the chamber from the fluid introduction port and through at least one of the first and second ports to allow other constituents to move away from the agents on the porous substrate,
wherein the controller is configured to reduce the second flow relative to the first flow to direct agents towards the porous substrate when agents are introduced to the chamber through the fluid introduction port.

14. A system for separating agents from non-agents in a chamber, the system comprising:
a chamber with a substantially truncated cone shape, the chamber comprising:
a fluid introduction port;
a porous substrate positioned substantially opposite from the fluid introduction port in the chamber, the porous substrate configured to prevent the passage of agents that are larger than a threshold size of the porous substrate, the porous substrate having a first side and a second side, wherein the fluid introduction port is positioned on the first side of the porous substrate;
a plurality of ports coupled to the chamber and configured to permit fluid to exit the chamber, wherein the plurality of ports includes at least a first port, a second port and a third port, wherein the first port and the second port are positioned on the first side of the porous substrate and the third port is positioned on the second side of the porous substrate;
a controller configured to control:
a first flow of fluid into the chamber from the fluid introduction port and through the porous substrate to hold agents and other constituents at the porous substrate; and
a second flow of fluid into the chamber from the fluid introduction port and through at least one of the first and second ports to allow other constituents to move away from the agents on the porous substrate, wherein the controller is configured to increase the second flow relative to the first flow to move other constituents away from the agents on the porous substrate.

* * * * *